US012788291B2

(12) United States Patent
Okamoto et al.

(10) Patent No.: US 12,788,291 B2
(45) Date of Patent: Nov. 10, 2026

(54) EMOTION ESTIMATING DEVICE, EMOTION ESTIMATING SYSTEM, AND EMOTION ESTIMATING METHOD

(71) Applicant: ASICS CORPORATION, Kobe (JP)

(72) Inventors: Toshiaki Okamoto, Kobe (JP); Ken Kusano, Kobe (JP); Shunsuke Yamagata, Kobe (JP); Masaru Ichikawa, Kobe (JP); Satoru Abe, Kobe (JP)

(73) Assignee: ASICS CORPORATION, Kobe (JP)

( * ) Notice: Subject to any disclaimer, the term of this patent is extended or adjusted under 35 U.S.C. 154(b) by 323 days.

(21) Appl. No.: 18/456,767

(22) Filed: Aug. 28, 2023

(65) Prior Publication Data

US 2024/0065600 A1 Feb. 29, 2024

(30) Foreign Application Priority Data

Aug. 29, 2022 (JP) ................................ 2022-136122
Dec. 14, 2022 (JP) ................................ 2022-199705

(51) Int. Cl.
*A61B 5/16* (2006.01)
*A61B 5/00* (2006.01)
(Continued)

(52) U.S. Cl.
CPC .............. *A61B 5/165* (2013.01); *A61B 5/112* (2013.01); *A61B 5/6807* (2013.01); *G16H 10/20* (2018.01);
(Continued)

(58) Field of Classification Search
CPC . A61B 5/112; A61B 2562/0219; A61B 5/165; G16H 20/30; G06N 5/04
See application file for complete search history.

(56) References Cited

U.S. PATENT DOCUMENTS 9,189,471 B2 * 11/2015 Kim ...................... A61B 5/165
2010/0329529 A1 * 12/2010 Feldman ........... G06F 18/21375 382/131

(Continued)

FOREIGN PATENT DOCUMENTS

CN 111643098 A 9/2020
CN 111904441 A 11/2020

(Continued)

OTHER PUBLICATIONS

Identifying Emotions from Walking Using Affective and Deep Features, Randhavane et al. arXiv:1906.11884v4 [cs.CV] Jan. 9, 2020 (Year: 2020).*

(Continued)

*Primary Examiner* — Sean P Dougherty
(74) *Attorney, Agent, or Firm* — Studebaker Brackett PLLC

(57) ABSTRACT

An emotion estimating device, an emotion estimating system, and an emotion estimating method capable of estimating an emotion of a subject based on information obtained from daily activities can be provided. An emotion estimating device includes an interface that receives input of walking data of a subject measured by a measurement device and emotion data obtained by quantifying the emotion of the subject, a storage that stores the walking data and the emotion data, and an computer that obtains corresponding data in which a plurality of walking parameters included in the walking data stored in the storage are associated with the emotion data. When the interface newly receives the input of the walking data, the computer estimates the emotion of the subject from the plurality of walking parameters included in the newly received walking data, and outputs information indicating the estimated emotion of the subject.

9 Claims, 20 Drawing Sheets

(51) Int. Cl.

| | |
|---|---|
| ***A61B 5/11*** | (2006.01) |
| ***G06N 5/04*** | (2023.01) |
| ***G16H 10/20*** | (2018.01) |
| ***G16H 20/30*** | (2018.01) |
| ***G16H 50/70*** | (2018.01) |

(52) U.S. Cl.

CPC ............. *G16H 20/30* (2018.01); *G16H 50/70* (2018.01); *A61B 2562/0219* (2013.01); *G06N 5/04* (2013.01)

(56) References Cited

U.S. PATENT DOCUMENTS

| | | | | |
|---|---|---|---|---|
| 2013/0132088 | A1* | 5/2013 | Kim | A61B 5/165 704/270 |
| 2017/0105662 | A1* | 4/2017 | Silawan | A61B 5/14542 |
| 2017/0143246 | A1* | 5/2017 | Flickinger | A61B 5/6898 |
| 2018/0032126 | A1* | 2/2018 | Liu | G06V 10/143 |
| 2018/0132776 | A1* | 5/2018 | Flickinger | A63F 13/25 |
| 2019/0239795 | A1 | 8/2019 | Kotake et al. | |
| 2021/0145340 | A1 | 5/2021 | Asukai | |
| 2021/0401338 | A1* | 12/2021 | Flickinger | G16H 40/63 |

FOREIGN PATENT DOCUMENTS

| | | | | | |
|---|---|---|---|---|---|
| CN | 112515675 | A | * | 3/2021 | A61B 5/1116 |
| CN | 114504320 | A | * | 5/2022 | A61B 7/7264 |
| FR | 2961085 | A1 | * | 12/2011 | G16H 20/70 |
| JP | 2017-144222 | A | | 8/2017 | |
| JP | 2018-102617 | A | | 7/2018 | |
| JP | 6388824 | B2 | | 9/2018 | |
| JP | 2019-017946 | A | | 2/2019 | |
| JP | 2020-120908 | A | | 8/2020 | |
| KR | 10-2021-0084779 | A | | 7/2021 | |
| KR | 20210084779 | A | * | 7/2021 | G16H 20/70 |
| WO | WO-2017065694 | A1 | * | 4/2017 | A61B 5/165 |
| WO | WO-2018158704 | A1 | * | 9/2018 | A61B 5/318 |
| WO | WO-2019089652 | A1 | * | 5/2019 | G16H 40/67 |
| WO | WO-2019207896 | A1 | * | 10/2019 | A61B 5/0077 |
| WO | WO-2021248916 | A1 | * | 12/2021 | A61B 5/7267 |

OTHER PUBLICATIONS

Normative spatiotemporal gait parameters in older adults, Hollman et al., Gait & Posture 34 (2011) 111-118, 2011 (Year: 2011).*

How we walk affects what we remember: Gait modifications through biofeedback change negative affective memory bias, Michalak et al., J. Behav. Ther. & Exp. Psychiat. 46 (2015) 121e125 (Year: 2015).*

Zhao et al., "See your mental state from your walk: Recognizing anxiety and depression through Kinect-recorded gait data", Published: May 22, 2019, PLOS | One, pp. 1-13 (Year: 2019).*

Karg et al., "Recognition of Affect Based on Gait Patterns" Aug. 2010, IEEE, vol. 40, pp. 1050-1060 (Year: 2010).*

J. P. Bader et al., "Muskelkraft und Gangcharakteristika depressiver Menschen", Der Nervenarzt, vol. 70, No. 7, Jul. 1, 1999, XP055004007, pp. 613-619; with partial English translation.

The extended European search report issued by the European Patent Office on Jan. 25, 2024, which corresponds to European Patent Application No. 23190521.7-1113 and is related to U.S. Appl. No. 18/456,767.

"Notice of Reasons for Refusal" Office Action issued in JP 2022-199705; mailed by the Japanese Patent Office on Aug. 12, 2026.

* cited by examiner

FIG.8

R1

| | DELIGHTED | DEPRESSED | IRRITATED | CONTROL |
|---|---|---|---|---|
| STRIDE [m] | 1.42(0.10) | *1.39(0.11) | 1.41(0.09) | 1.41(0.10) |
| PITCH [step/s] | 0.98(0.05) | 0.98(0.06) | **1.01(0.08) | 0.97(0.05) |
| WALKING SPEED [m/s] | *1.40(0.14) | 1.36(0.15) | **1.44(0.16) | 1.37(0.14) |
| TIME REQUIRED FOR ONE STEP [s/step] | 1.03(0.05) | 1.04(0.07) | **1.00(0.08) | 1.04(0.05) |
| STANCE PHASE PERIOD [s] | 0.65(0.05) | 0.66(0.06) | **0.64(0.07) | 0.66(0.05) |
| SWING PHASE PERIOD [s] | 0.38(0.02) | 0.38(0.02) | **0.37(0.02) | 0.38(0.02) |
| TOE UPWARD ANGLE AT TIME OF LANDING [deg] | −20.20(4.26) | −19.16(3.73) | −20.50(3.36) | −20.00(3.89) |
| HEEL UPWARD ANGLE AT TIME OF LEAVING [deg] | −64.50(4.83) | *−63.74(5.36) | −64.60(4.54) | −64.80(5.29) |
| PRONATION [deg] | −7.60(4.12) | *−8.01(4.08) | −7.09(4.17) | −7.01(4.78) |
| MAXIMUM FOOT UPWARD HEIGHT [m] | 0.12(0.01) | 0.12(0.01) | 0.12(0.01) | 0.12(0.01) |
| MAXIMUM VALUE OF ACCELERATION IN VERTICAL DIRECTION AT TIME OF LANDING [$m/s^2$] | 39.60(6.06) | 38.76(6.12) | 38.70(4.45) | 38.50(5.78) |

FIG.9

R2

| | PC1 | PC2 | PC3 |
|---|---|---|---|
| STRIDE [m] | 0.158 | −0.525 | 0.121 |
| PITCH [step/s] | −0.5 | −0.0153 | −0.0782 |
| WALKING SPEED [m/s] | −0.308 | −0.44 | 0.0631 |
| TIME REQUIRED FOR ONE STEP [s/step] | 0.487 | −0.00516 | −0.113 |
| STANCE PHASE PERIOD [s] | 0.486 | 0.079 | 0.02 |
| SWING PHASE PERIOD [s] | 0.0746 | −0.33 | −0.535 |
| TOE UPWARD ANGLE AT TIME OF LANDING [deg] | −0.0559 | 0.526 | −0.0917 |
| HEEL UPWARD ANGLE AT TIME OF LEAVING [deg] | −0.214 | 0.0446 | −0.567 |
| PRONATION [deg] | 0.262 | −0.28 | −0.0591 |
| MAXIMUM FOOT UPWARD HEIGHT [m] | −0.0507 | −0.155 | −0.356 |
| MAXIMUM VALUE OF ACCELERATION IN VERTICAL DIRECTION AT TIME OF LANDING [m/s$^2$] | −0.178 | −0.186 | 0.464 |

FIG.11

R3

| | COEFFICIENT |
|---|---|
| INTERCEPT | 8.171642 |
| STRIDE [m] | −5.5574 |
| PITCH [step/s] | −3.93334 |
| WALKING SPEED [m/s] | 8.312544 |
| TIME REQUIRED FOR ONE STEP [s/step] | 0 |
| STANCE PHASE PERIOD [s] | 1.315231 |
| SWING PHASE PERIOD [s] | 0.225688 |
| TOE UPWARD ANGLE AT TIME OF LANDING [deg] | −0.36146 |
| HEEL UPWARD ANGLE AT TIME OF LEAVING [deg] | 0.417201 |
| PRONATION [deg] | 0.547711 |
| MAXIMUM FOOT UPWARD HEIGHT [m] | 0.574167 |
| MAXIMUM VALUE OF ACCELERATION IN VERTICAL DIRECTION AT TIME OF LANDING [$m/s^2$] | 0.561674 |

EMOTION ESTIMATING DEVICE, EMOTION ESTIMATING SYSTEM, AND EMOTION ESTIMATING METHOD

CROSS REFERENCE TO RELATED APPLICATIONS

This nonprovisional application is based on Japanese Patent Application No. 2022-136122 filed on Aug. 29, 2022, and Japanese Patent Application No. 2022-199705 filed on Dec. 14, 2022, with the Japan Patent Office, the entire contents of which are hereby incorporated by reference.

BACKGROUND

Technical Field

The present disclosure relates to an emotion estimating device, an emotion estimating system, and an emotion estimating method.

Description of the Background Art

In recent years, not only health of body but also health of heart are desired. However, even when the health of the body can be quantified by a health examination or the like, it is difficult to quantify the health of the heart, and means and a method for visualizing a state (emotion) of the heart are studied every day. In addition, the state of the body (physical condition) becomes apparent as a symptom and is easily perceived by the person in question, and the surrounding person also easily notices the state of the body. However, because the state of the heart does not become apparent as a symptom unlike the physical condition, the surrounding person also hardly notices the state of the heart, and even the person in question does not easily notice the state of the heart. For this reason, there is a case where the state of the heart remains in an unsatisfactory state, detection of the state of the heart is delayed and becomes serious, leading to a mental disease such as depression, and it is a social problem to keep the physical state healthy.

Accordingly, there is a great demand for visualizing the state (emotion) of the heart, and there is a greater demand when a method for estimating the state of the heart is simple. For example, Japanese Patent Laying-Open No. 2020-120908 discloses a mental state estimating system that extracts an expression index of a subject from an image obtained by capturing an expression of the subject and estimates a mental state of the subject based on the extracted expression index. Japanese Patent Laying-Open No. 2019-017946 discloses a mood estimating system that estimates a variation amount of a mood of the subject based on biological information in a resting state and biological information in a non-resting state. Furthermore, Japanese Patent No. 6388824 discloses an emotion information estimating device that stores the biological information of the subject and emotion information and a physical state of the user corresponding to the biological information, learns a relationship between the biological information and the emotion information, and estimates the emotion information from the biological information for each physical state. Japanese Patent Laying-Open No. 2017-144222 discloses an emotion estimating device that acquires physiological data and non-physiological data of the subject, calculates an awakening degree of the subject and a comfort degree of the subject, and estimates the emotion of the subject from the calculated values.

SUMMARY

In the disclosed device and method, in order to estimate the emotion of the subject, the image obtained by imaging the expression of the subject is required, or the biological information and physiological data of the subject are required. For this reason, in order to estimate the emotion of the subject, work of capturing the expression and acquiring the biological information and the physiological data is required to be performed, and it cannot be said that the emotion is estimated by the simple method. In particular, a device and a method for estimating the emotion of the subject based on information obtained from daily activities without causing the subject to perform special work are desired in order to estimate the emotion.

The present disclosure has been made to solve such a problem, and an object of the present disclosure is to provide an emotion estimating device, an emotion estimating system, and an emotion estimating method capable of estimating the emotion of the subject based on the information obtained from daily activities.

An emotion estimating device according to one aspect of the present disclosure is an emotion estimating device that estimates an emotion of a subject. The emotion estimating device includes: an interface that receives input of walking data of the subject measured by a measurement device and emotion data obtained by quantifying the emotion of the subject; a storage that stores the walking data and the emotion data received by the interface; and a computer that obtains corresponding data in which a plurality of walking parameters included in the walking data stored in the storage are associated with the emotion data. When the input of the walking data is newly received in the interface, the computer estimates the emotion of the subject from the plurality of walking parameters included in the newly received walking data based on the corresponding data, and outputs information indicating the estimated emotion of the subject from the interface.

An emotion estimating system according to one aspect of the present disclosure includes a measurement device that measures the walking data of the subject, and the above emotion estimating device.

An emotion estimating method according to one aspect of the present disclosure is an emotion estimating method for estimating an emotion of a subject. The emotion estimating method includes: receiving input of walking data of the subject measured by a measurement device and emotion data obtained by quantifying the emotion of the subject; storing the input walking data and the input emotion data in a storage; obtaining corresponding data in which a plurality of walking parameters included in the walking data stored in the storage are associated with the emotion data; when the input of the walking data is newly received, estimating the emotion of the subject from the plurality of walking parameters included in the newly received walking data based on the corresponding data; and outputting information indicating the estimated emotion of the subject.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 8 is a view illustrating an example of a relationship between a walking parameter and emotion data in the emotion estimating device of the first embodiment.

FIG. 9 is a view illustrating an example of main component analysis in the emotion estimating device of the first embodiment.

FIG. 11 is a view illustrating an example of multiple regression analysis in the emotion estimating device of the first embodiment.

DESCRIPTION OF THE PREFERRED EMBODIMENTS

Figure 1:
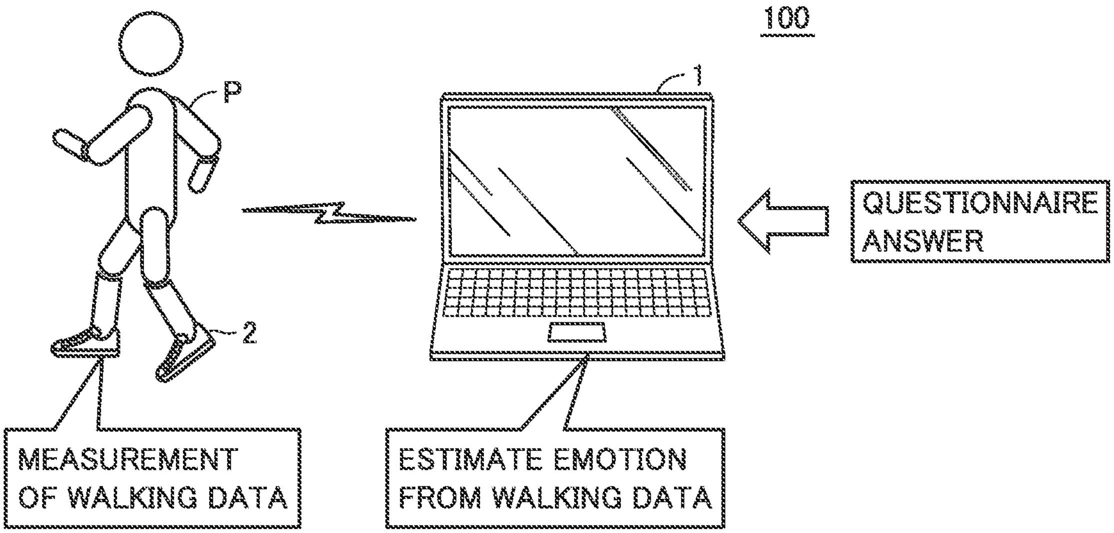
FIG. 1 is a schematic diagram illustrating a configuration of an emotion estimating system including the emotion estimating device according to a first embodiment.

The present disclosure provides an emotion estimating device, an emotion estimating system, and an emotion estimating method that focus on a relationship between a state of a heart and a gait and specify the gait of a subject from walking data to estimate an emotion of the subject. Therefore, in the emotion estimating device, the emotion estimating system, and the emotion estimating method according to the present disclosure, the emotion from a simple motion such as walking in daily activities can be estimated. Hereinafter, embodiments will be described with reference to the drawings. In the following description, the same configuration is denoted by the same reference numeral. Names and functions of such components are also the same. Therefore, no redundant detailed description will be given of such components.

First Embodiment

[Configuration of Emotion Estimating System]

FIG. 1 is a schematic diagram illustrating a configuration of an emotion estimating system 100 including an emotion estimating device 1 according to a first embodiment. Emotion estimating system 100 includes emotion estimating device 1 that estimates emotion of a subject P from walking data and a measurement device 2 that measures the walking data of subject P. In order to estimate the emotion of subject P from the walking data, emotion estimating device 1 needs to previously obtain corresponding data in which a plurality of walking parameters included in the walking data are associated with the emotion data. In the present disclosure, an example in which the corresponding data is obtained from the walking data and the emotion data of a plurality of subjects P and then the emotion of subject P is estimated using the obtained corresponding data will be described. However, a configuration in which the corresponding data obtained by a large number of subjects is the accumulated and generalized corresponding data is prepared may be used. Alternatively, in a case where the generalized corresponding data is prepared for each attribute (for example, gender, age, and race) to estimate the emotion from the walking data of subject P using emotion estimating device 1, the appropriate corresponding data may be selected according to the attribute of subject P.

Figure 2:
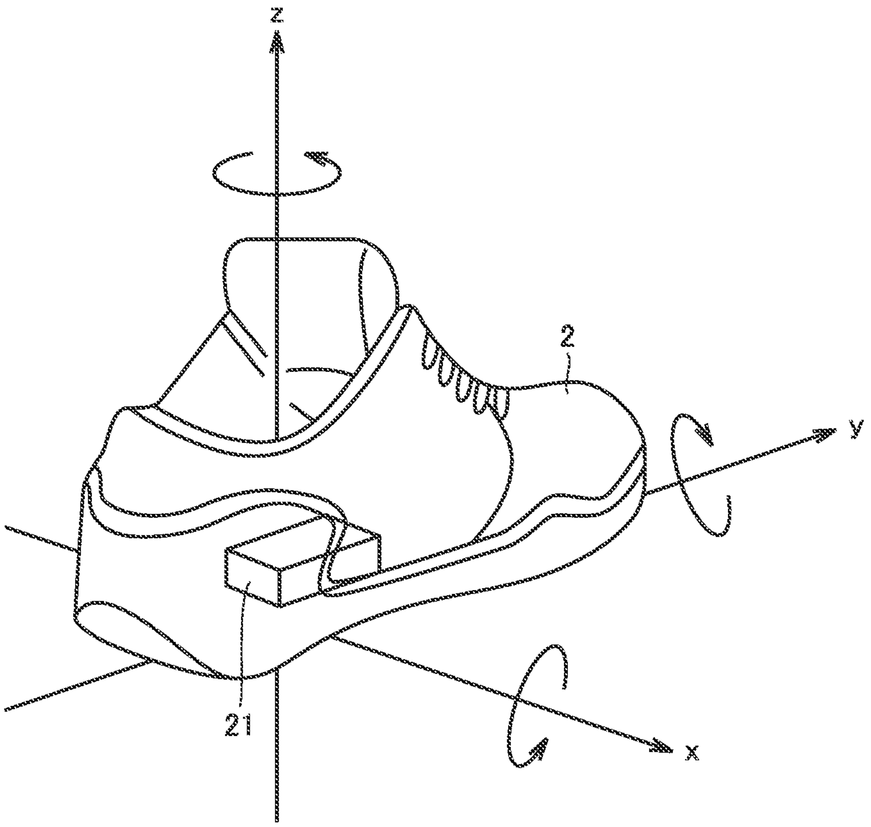
FIG. 2 is a schematic diagram for describing a measurement device of the first embodiment.

Although a method for obtaining the corresponding data will be described later, the walking data of subject P needs to be measured by measurement device 2 in order to obtain the corresponding data. In emotion estimating system 100 of FIG. 1, an example in which measurement device 2 is a smart shoe is illustrated. FIG. 2 is a schematic diagram for describing measurement device 2 of the first embodiment. FIG. 2 illustrates the smart shoe that is measurement device 2. A sensor module 21 is incorporated in the smart shoes, and measures the walking data of subject P.

Although not illustrated, sensor module 21 includes an acceleration sensor, an angular velocity sensor, an arithmetic circuit that operates a walking parameter from measurement values of these sensors, and a communication circuit that wirelessly transmits the walking parameter and the measurement value operated by the arithmetic circuit to emotion estimating device 1. For example, the acceleration sensor can measure accelerations of three axes of X, Y, Z, and the angular velocity sensor can measure angular velocities of the three axes of X, Y, Z. Consequently, in addition to the measurement value of the acceleration sensor and the measurement value of the angular velocity sensor, sensor module 21 can obtain the walking parameters of a stride, a pitch, a walking speed, time required for one step, a stance phase period, a swing phase period, a toe upward angle at time of landing, a heel upward angle at time of leaving, a pronation, a maximum foot upward height, and a maximum value of acceleration in a vertical direction at time of landing as the walking data of subject P. At this point, the maximum value of the acceleration in the vertical direction at the time of landing is an example of a walking parameter that evaluates impact (landing impact) applied to the foot at the time of landing. Examples of the walking parameter of the landing impact include a method for evaluating the landing impact by the vertical movement of the center of gravity of the head or the body, and a method for evaluating the landing impact by directly measuring floor reaction force with a force plate, a foot pressure mat, or the like.

Although it has been described that the data transfer such as the walking parameter from sensor module 21 to emotion estimating device 1 is performed by wireless communication, the present disclosure is not limited thereto. For example, the data transfer such as the walking parameter from sensor module 21 to emotion estimating device 1 may be performed by wired communication or by a recording medium (for example, a memory chip or a USB memory).

In addition, although it has been described that sensor module 21 operates the walking parameter from the measurement value of the acceleration sensor and the measurement value of the angular velocity sensor, the present disclosure is not limited thereto. For example, sensor module 21 may only transmit the measurement value of the acceleration sensor and the measurement value of the angular velocity sensor to emotion estimating device 1, or emotion estimating device 1 may operate the walking parameter from the measurement value of the acceleration sensor and the measurement value of the angular velocity sensor acquired from sensor module 21.

In the present disclosure, measurement device 2 will be described as the smart shoe. However, measurement device 2 that measures the walking data of subject P is not limited to the smart shoe. For example, measurement device 2 may be a portable device such as a three-dimensional posture recognition camera (for example, Kinect (registered trademark)) capable of recognizing the movement of the entire body including the foot of subject P, or a smartphone or a smart watch having an acceleration sensor and an angular velocity sensor.

In addition, in order to obtain corresponding data as illustrated in FIG. 1, an answer of a questionnaire about the emotion during the walking from subject P is needed to be received and the emotion data obtained by quantifying the emotion of subject P is needed to input to emotion estimating device 1. In the questionnaire, for example, subject P evaluates emotions on a 7-point scale, and quantifies the emotion. In addition, the questionnaire may be performed at timing to check whether the emotion of subject P is induced after emotion induction is performed on subject P as described later, in addition to the case where the emotion held by subject P during the walking is answered afterwards. Instead of performing the emotion induction, subject P may be caused to walk while being conscious of a specific emotion. In this case, subject P answers the questionnaire about the emotion felt by subject P.

In the present disclosure, it is described that emotion estimating system 100 including emotion estimating device 1 and measurement device 2 estimates the emotion of subject P from the walking data, but the configuration of the system is not limited thereto. For example, as the configuration of the system, measurement device 2 may be integrated with emotion estimating device 1, or emotion estimating device 1 may be integrated with measurement device 2. Specifically, a system in which the walking data of subject P is measured by a smartphone and the emotion of subject P is estimated from the walking data measured by the smartphone is conceivable as the system in which measurement device 2 is integrated with emotion estimating device 1. Furthermore, a system that measures the walking data of subject P with the smart shoes and estimating the emotion of subject P from the walking data measured with the smart shoes is conceivable as the system in which emotion estimating device 1 is integrated with measurement device 2.

[Configuration of Emotion Estimating Device]

Figure 3:
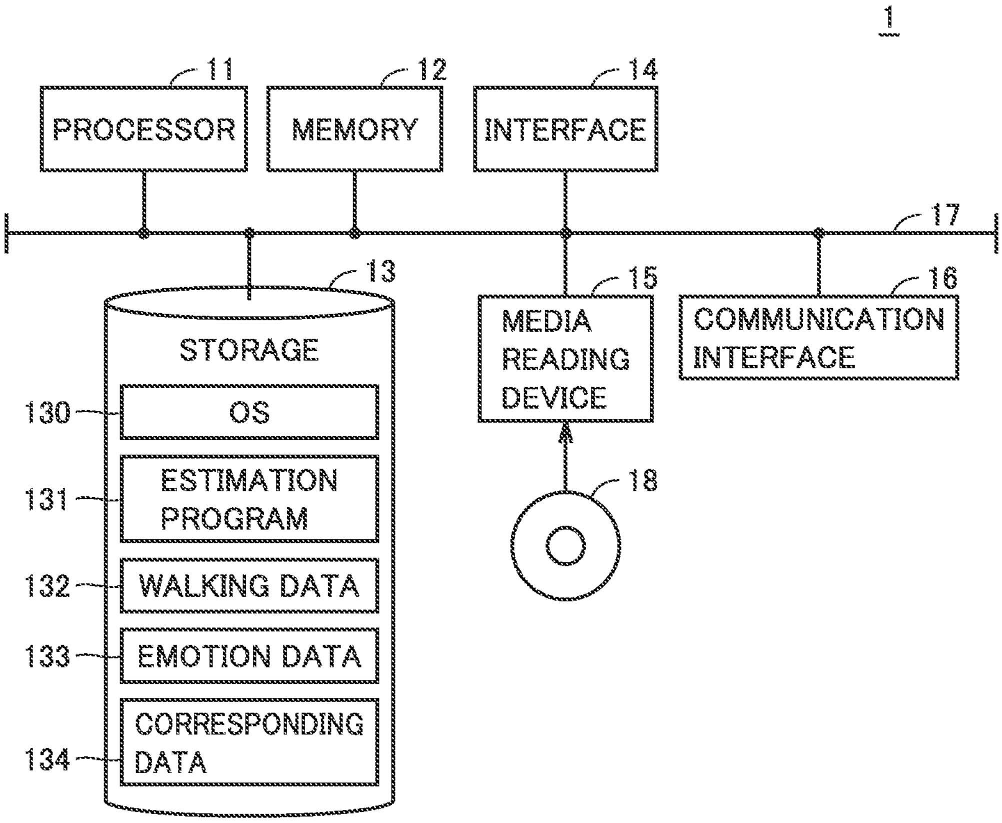
FIG. 3 is a block diagram illustrating a configuration of the emotion estimating device of the first embodiment.

FIG. 3 is a block diagram illustrating a configuration of emotion estimating device 1 of the first embodiment. As illustrated in FIG. 3, emotion estimating device 1 includes a processor 11, a memory 12, a storage 13, an interface 14, a media reading device 15, and a communication interface 16. These components are connected through a processor bus 17.

Processor 11 is an example of the "computer". Processor 11 is a computer that reads a program (for example, an operating system (OS) 130 and an estimation program 131) stored in storage 13, develops the read program in memory 12, and executes the program. For example, processor 11 includes a central processing unit (CPU), a field programmable gate array (FPGA), or a graphics processing unit (GPU), or a multi-processing unit (MPU). Processor 11 may be configured of processing circuitry.

Memory 12 includes a volatile memory such as a dynamic random access memory (DRAM) or a static random access memory (SRAM) or a nonvolatile memory such as a read only memory (ROM) or a flash memory.

Storage 13 is an example of the "storage". Storage 13 is configured of a nonvolatile storage device such as a solid state drive (SSD) and a hard disk drive (HDD). In addition to OS 130 and estimation program 131, storage 13 stores walking data 132, emotion data 133, corresponding data 134, and the like.

Estimation program 131 is a program that executes processing for estimating the emotion of subject P from walking data 132 (estimation processing II in FIG. 4 described later). Estimation program 131 may include a program that executes processing (preparation processing I in FIG. 4 described later) for obtaining corresponding data 134 in which walking data 132 and emotion data 133 are associated with each other as pre-processing for performing the processing for estimating the emotion of subject P from walking data 132.

Walking data 132 includes the acceleration and angular velocity measured by measurement device 2 and the walking parameter calculated from these measured values. The input of walking data 132 is received from measurement device 2 through communication interface 16, and stored in storage 13.

Emotion data 133 includes quantified data obtained by evaluating the emotion of subject P in a 7-point scale questionnaire. The input of emotion data 133 is received through interface 14, and stored in storage 13.

Corresponding data 134 is data in which walking data 132 and emotion data 133 are associated with each other, and for example, includes data of an analysis result obtained by performing main component analysis, a multiple regression equation obtained by performing multiple regression analysis, and data of a coefficient of an explanatory variable. That is, corresponding data 134 may include data required for estimating the emotion of subject P from newly received walking data 132.

Interface 14 is an example of the "interface", the "input circuitry", and the "output circuitry". When subject P operates a keyboard, a mouse, a touch device, and the like, interface 14 receives the input of the emotion data 133 answered in the questionnaire by. Interface 14 also outputs information indicating the estimated emotion of subject P to a display, a speaker, or the like.

Media reading device 15 receives a storage medium such as a removable disk 18, a memory chip, or a USB memory, and acquires data stored in removable disk 18, the memory chip, the USB memory, or the like.

Communication interface 16 is an example of the "interface", the "input circuitry", and the "output circuitry". Communication interface 16 transmits and receives the data to and from measurement device 2 or another device by performing wired communication or wireless communication. For example, communication interface 16 communicates with measurement device 2 to receive the input of walking data 132 measured by measurement device 2. Communication interface 16 may output information indicating the estimated emotion of subject P to another device by communicating with the other device.

Although it has been described that emotion estimating device 1 obtains corresponding data 134 from walking data 132 and emotion data 133, the corresponding data may be received from a server or the like through communication interface 16 as long as generalized corresponding data 134 is previously prepared. Emotion estimating device 1 may read corresponding data 134 stored in removable disk 18 or the like by media reading device 15.

[Emotion Estimation Processing]

With reference to a flowchart of the emotion estimation processing executed by emotion estimating device 1, processing for estimating the emotion of subject P from walking data 132 will be described. FIG. 4 is a flowchart for describing emotion estimation processing executed by emotion estimating device 1 of the first embodiment. Processor 11 of emotion estimating device 1 executes estimation program 131 to implement each step in FIG. 4.

In order to estimate the emotion of subject P from walking data 132, emotion estimating device 1 needs to previously obtain corresponding data 134 in which a plurality of walking parameters included in walking data 132 are associated with emotion data 133. For this reason, as preprocessing for performing processing for estimating the emotion of subject P from walking data 132, emotion estimating device 1 executes preparation processing I for obtaining corresponding data 134 in which walking data 132 and emotion data 133 are associated with each other as illustrated in FIG. 4.

Figure 5:
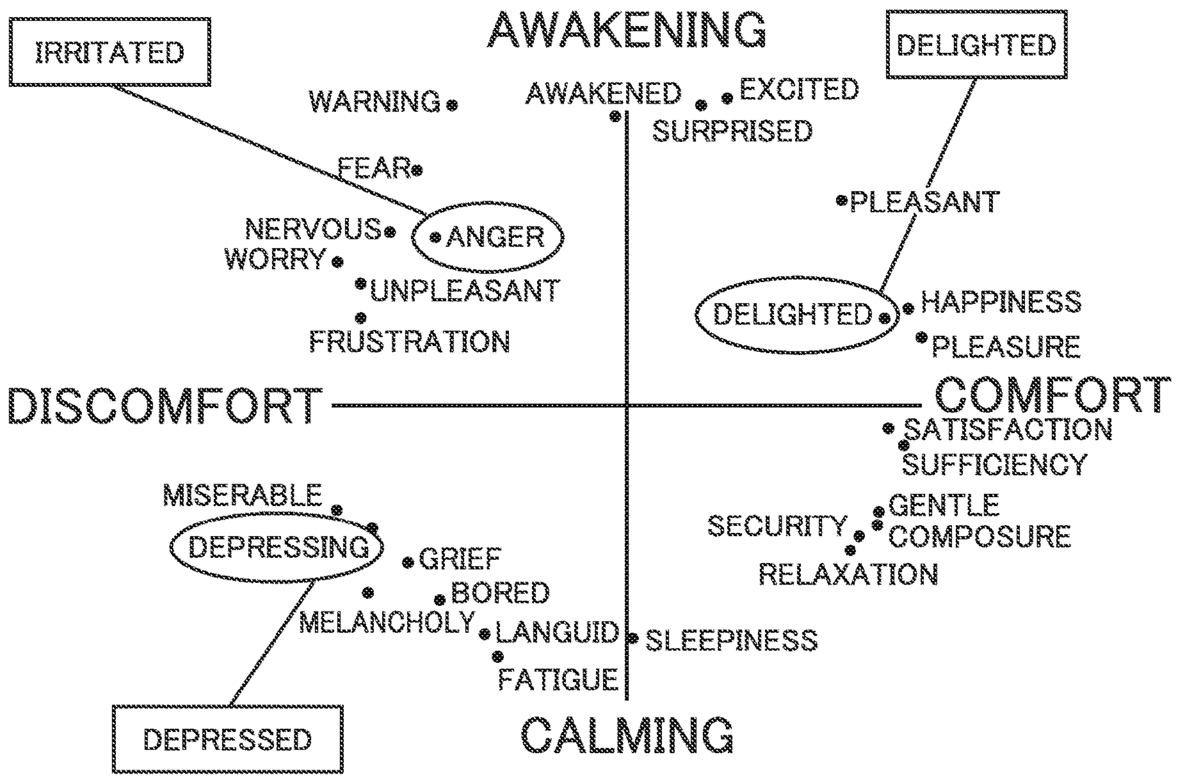
FIG. 5 is a schematic diagram in which emotions are classified using a Russell's circumplex model.

In preparation processing I, in order to obtain corresponding data 134, after the emotion induction that inspires the specific emotion to subject P is performed, subject P is caused to walk, and walking data 132 is measured by measurement device 2. For example, human emotions can be classified using a Russell's circumplex model. FIG. is a schematic diagram in which emotions are classified using a Russell's circumplex model. As illustrated in FIG. 5, in the Russell's circumplex model, emotions such as "delighted", "anger", and "depressing" are expressed by two axes of "comfort –discomfort" and "awakening–calming" and mapped on a two-dimensional coordinate plane. In the present embodiment, the emotion induction is performed on subject P, assuming that the emotion of a portion of the Russell's circumplex model that feels "delighted" is "delighted", the emotion of a portion of the Russell's circumplex model that feels "depressing" is "depressed", and the emotion of a portion of the Russell's circumplex model that feels "anger" is "irritated".

In preparation processing I, before the emotion induction is performed on subject P, processing a for causing subject P to walk in a normal state (control state) in which the emotion induction is not performed and measuring walking data 132 by measurement device 2 is performed. In processing a in FIG. 4, emotion estimating device 1 receives the input of the questionnaire answered from subject P in the normal state in which the emotion induction is not performed (step S101). The questionnaire performed in step S101 is the same as the questionnaire performed in the emotion induction state (see FIG. 7). Furthermore, by causing subject P to walk a predetermined distance (for example, 5 m) twice while wearing the smart shoes of measurement device 2, emotion estimating device 1 receives the input of the walking data measured in the walking (step S102).

Figure 6:
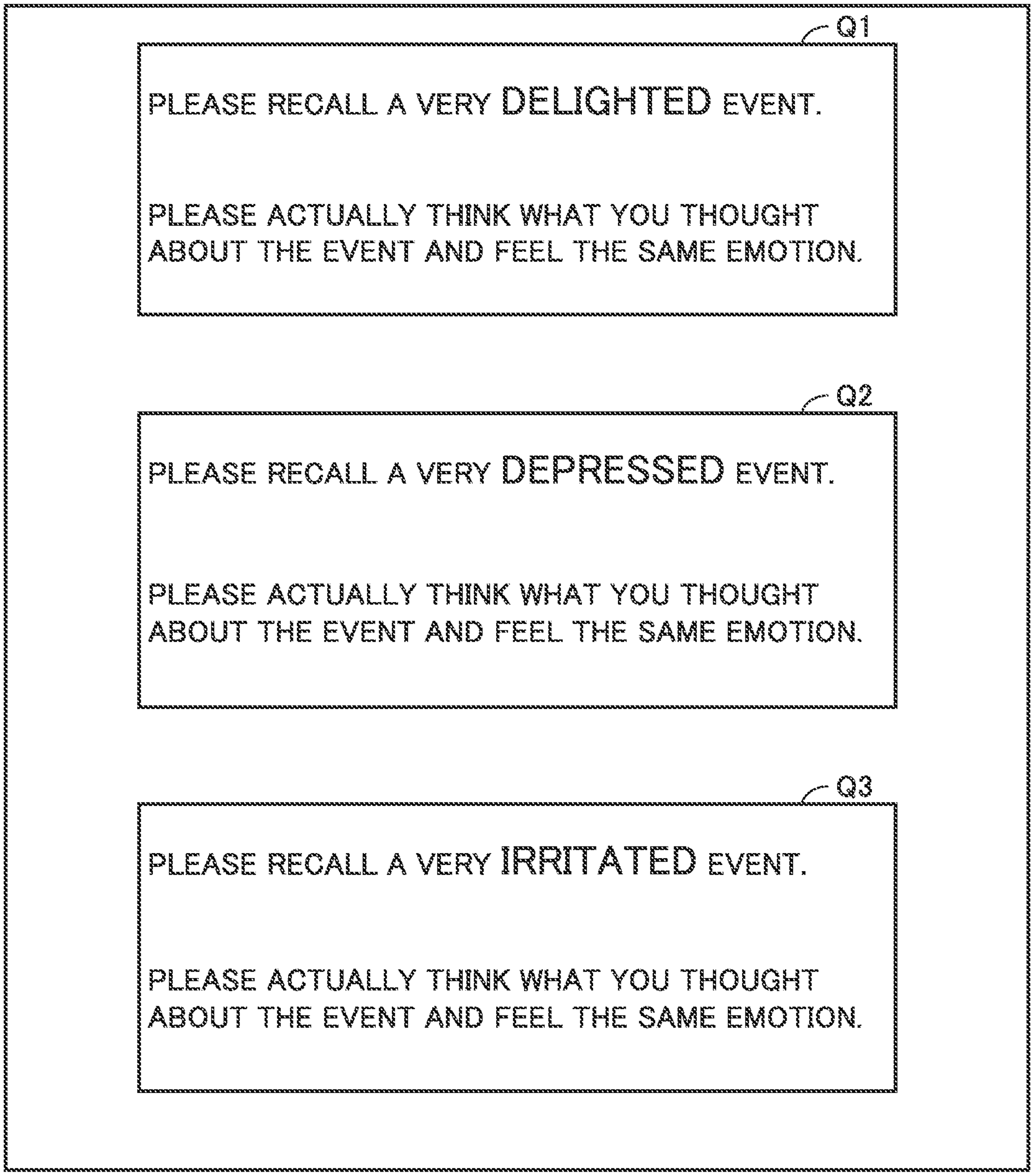
FIG. 6 is a view illustrating an example of an emotion induction problem that performs emotion induction.

In preparation processing I, after processing a for measuring walking data 132 in the normal state in which the emotion induction is not performed, processing b for measuring walking data 132 in the emotion induction state is performed. In the present embodiment, an emotion induction problem that evokes past experiences is set for each of three emotions of "delighted", "depressed", and "irritated" that perform the emotion induction. FIG. 6 is a view illustrating an example of an emotion induction problem that performs emotion induction. An emotion induction problem Q1 is a problem that evokes the past experiences in order to induce the "delighted" emotion, and a sentence that "Please recall a very delighted event. Please actually think what you thought about the event and feel the same emotion." is described.

An emotion induction problem Q2 is a problem that evokes the past experiences in order to induce the "depressed" emotion, and a sentence that "Please recall a very depressed event. Please actually think what you thought about the event and feel the same emotion." is described.

An emotion induction problem Q3 is a problem that evokes the past experience in order to induce the "irritated" emotion, and a sentence that "Please recall a very irritated event. Please actually think what you thought about the event and feel the same emotion." is described. Although the example in which emotion induction problems Q1 to Q3 are sentences read by subject P has been described, the present disclosure is not limited thereto, and the emotion induction problems Q1 to Q3 may be voices, images, moving images, or the like.

Figure 7:
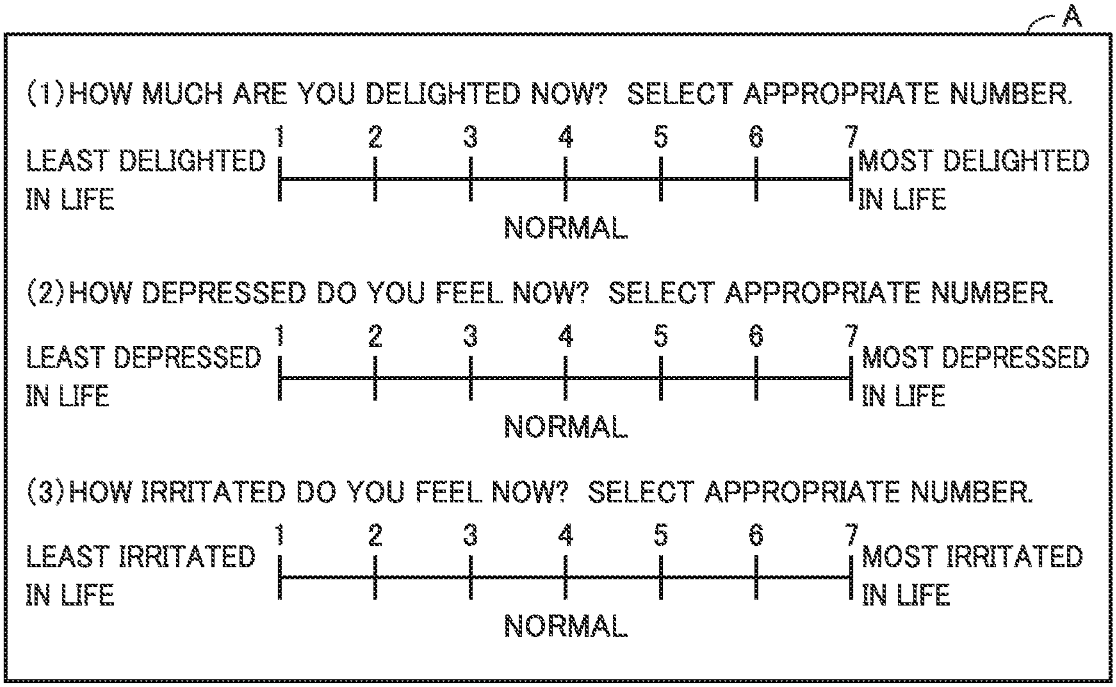
FIG. 7 is a view illustrating an example of a questionnaire that quantifies the emotion.

After subject P is induced to the emotion by reading one of the sentences of the emotion induction problems Q1 to Q3, subject P answers the questionnaire that evaluates the emotion using the seven-point scale in order to check how much the emotion is induced. FIG. 7 is a view illustrating an example of a questionnaire A that quantifies the emotion. In a questionnaire A in FIG. 7, in response to a question (1) "How much are you delighted now? Select appropriate number.", the least delighted case in life is answered as "1 point", the most delighted case in life is answered as "7 points", and the normal case is answered as "4 points". In addition, in questionnaire A in FIG. 7, in response to a question (2) "How depressed do you feel now? Select appropriate number.", the least depressed case in life is answered as "1 point", the most depressed case in life is answered as "7 points", and the normal case is answered as "4 points". Furthermore, in questionnaire A in FIG. 7, in response to a question (3) "How irritated do you feel now? Select appropriate number.", the least irritated case in life is answered as "1 point", the most irritated case in life is answered as "7 points", and the normal case is answered as "4 points".

Figure 4:
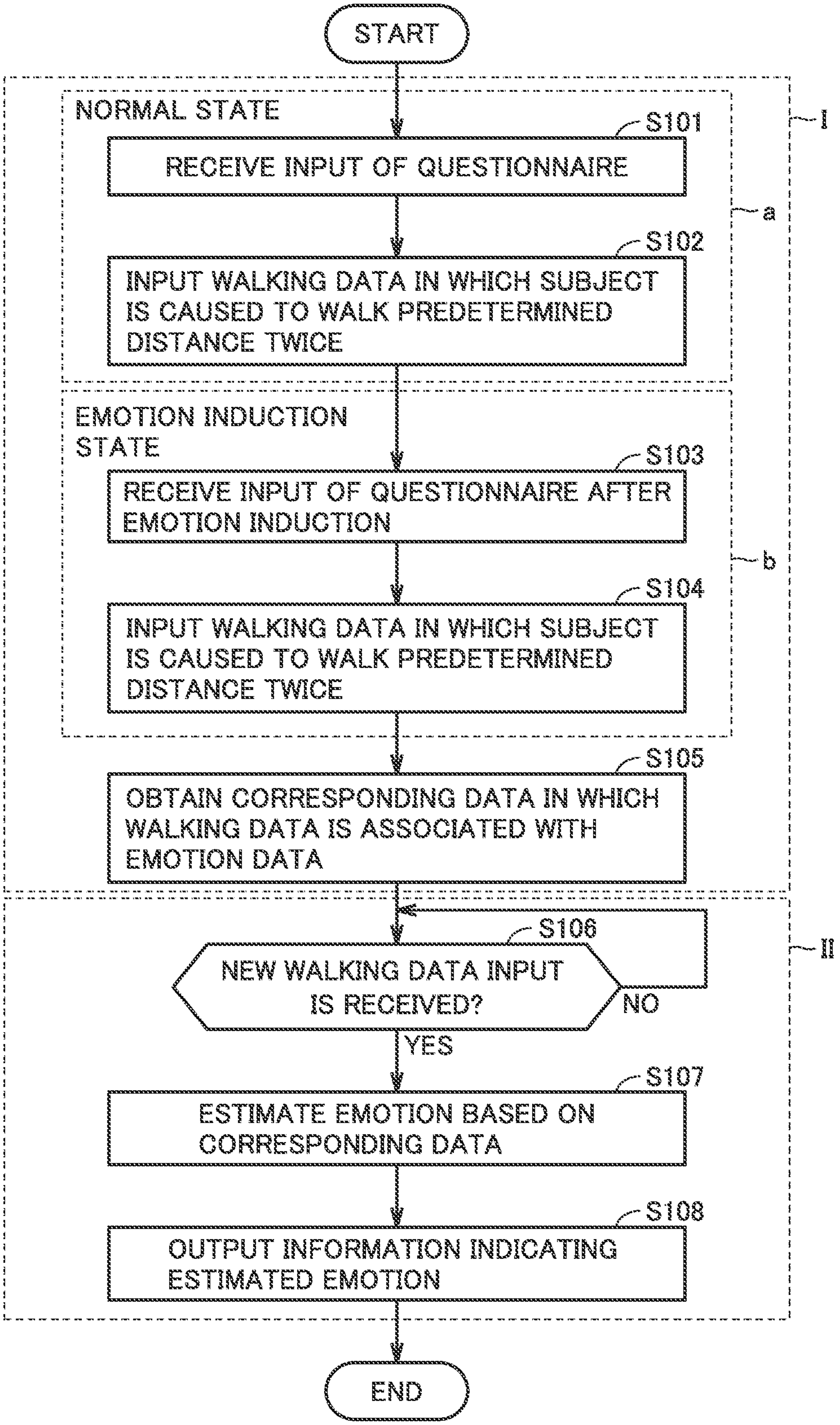
FIG. 4 is a flowchart for describing emotion estimation processing executed by the emotion estimating device of the first embodiment.

In process b in FIG. 4, emotion estimating device 1 receives the input of questionnaire A answered from subject P in the emotion induction state (step S103). Furthermore, by allowing subject P to walk (for example, twice) a predetermined distance (for example, 5 m) by wearing the smart shoes of measurement device 2, emotion estimating device 1 receives the input of walking data measured in the walking (step S104). The predetermined distance and the number of times of walking are examples, and for example, the predetermined distance may be 3 m or 10 m, and the number of times of walking may be 1 time or 3 times. The processing in steps S103 to S104 is performed on the same subject P for each of the three emotions of "delighted", "depressed", and "irritated", and the order of the induced emotions is random for each subject P. Questionnaire A in FIG. 7 is an example, but is not limited to the questionnaire that evaluates emotions using the 7-point scale. For example, questionnaire A may be a questionnaire that evaluates emotions using a 5-point scale or a 9-point scale.

Emotion estimating device 1 obtains the corresponding data in which walking data 132 and emotion data 133 acquired in processing a and processing b in FIG. 4 are associated with each other (step S105). Specifically, the processing for associating 18 (10 males and 8 females) healthy subjects P in their twenties to fifties will be described based on acquired walking data 132 and emotion data 133. FIG. 8 is a view illustrating an example of a relationship between the walking parameter and the emotion data in emotion estimating device 1 of the first embodiment. FIG. 8 illustrates data R1 indicating an average value and a standard deviation (numerical values in parentheses) of each walking parameter in each emotion.

From data R1, it can be seen that there is a tendency in a change in the walking parameter due to the induced emotion. For example, in the case where the emotion is "irritated", a significant difference can be found in the values of many walking parameters as compared with the case of the control state. Specifically, in the case where the emotion is "irritated", the "pitch" increases, the "walking speed" increases, the "time required for one step" decreases, the "stance phase period" decreases, and the "swing phase period" decreases. For these walking parameters, it is determined that there is a significant difference in a statistical temporary test with a significance level of 5%. In data R1, values assigned with two asterisks (**) are values determined to have a significant difference in the statistical temporary test with the significance level of 5%.

Furthermore, in the case where the emotion is "delighted", the "walking speed" increases. When the emotion is "depressed", the "stride" decreases, the "heel upward angle at time of leaving" decreases, and the "pronation" increases. For these walking parameters, it is determined that there is the significant difference in the statistical temporary test with the significance level of 10%. In data R1, a value assigned with one asterisk (*) is a value determined to have the significant difference in the statistical temporary test with the significance level of 10%.

The walking motion is not a motion in which each walking parameter independently changes, but is a motion in which each walking parameter mutually affects and changes. Accordingly, the main component analysis is applied to a plurality of walking parameters, and a tendency exerted on the plurality of walking parameters for each emotion is analyzed. At this point, the main component analysis is one of statistical methods for synthesizing a variable (main component) that represents the most variation of the whole with a small number of uncorrelated variables from a large number of correlated variables and dimensionally compressing the same. FIG. 9 is a view illustrating an example of the main component analysis in emotion estimating device 1 of the first embodiment. FIG. 9 illustrates data R2 obtained by performing the main component analysis on walking data 132 and emotion data 133 acquired from 18 subjects P.

In data R2, a factor load amount of each walking parameter in three main components PC1, PC2, PC3 is illustrated. At this point, the factor load amount is a correlation coefficient between each walking parameter and the main components PC1, PC2, PC3. Focusing on main component PC2 in data R2, the absolute value of the correlation coefficient is as high as 0.4 or more in the three walking parameters of "stride", "walking speed", and "toe upward angle at time of landing". Because three walking parameters indicates any negative correlation, it can be seen that the smaller the "stride", the slower the "walking speed", and the smaller the "toe upward angle at time of landing", the larger the value of main component PC2. From these relationships, newly synthesized main component PC2 can be interpreted as a variable representing "walking with small motion".

Figure 10:
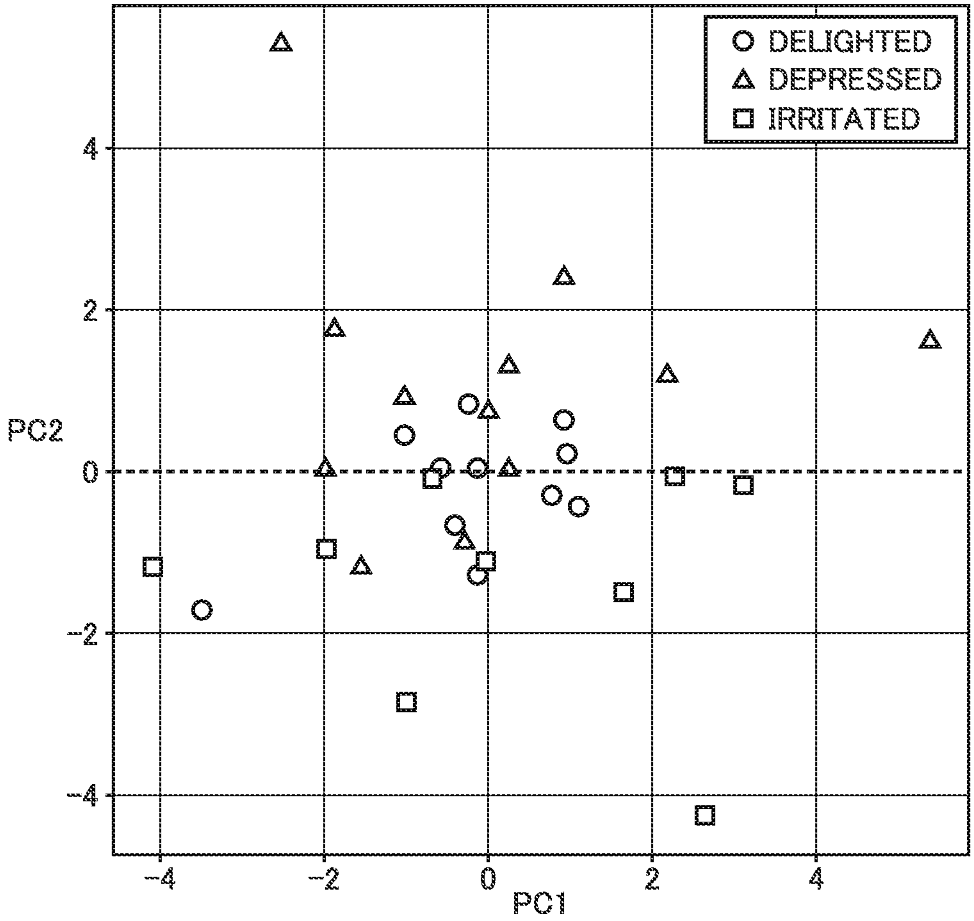
FIG. 10 is a view illustrating an example in which the main component analysis in FIG. 9 is graphed.

FIG. 10 is a view illustrating an example in which the main component analysis in FIG. 9 is graphed. FIG. 10 illustrates a graph in which emotion data 133 is plotted with main component PC1 on the horizontal axis and main component PC2 on the vertical axis. In the graph of FIG. 10, emotion data 133 of the "delighted" emotion is plotted by a circle, emotion data 133 of the "depressed" emotion is plotted by a triangle, and emotion data 133 of the "irritated" emotion is plotted by a square.

Although a broken line is drawn at a position where the value of main component PC2 is 0 (zero), many pieces of emotion data 133 of the "delighted" emotion are plotted around the broken line. Furthermore, many pieces of emotion data 133 of the "depressed" emotion of are plotted in the positive range of the value of main component PC2, and many pieces of emotion data 133 of the "irritated" emotion are plotted in the negative range of the value of main component PC2. Therefore, from the graph in FIG. 10, it can be seen that the emotion changes in the order of "irritated", "delighted", and "depressed" as the value of main component PC2 increases. That is, by adopting main component PC2 as corresponding data 134, the emotions of "irritated", "delighted", and "depressed" can be estimated from walking data 132.

Because the emotion changes to "irritated", "delighted", "depressed" due to the change in the value of main component PC2, it is considered that scoring can be performed on the axis of "comfort-discomfort" of the Russell's circumplex model in FIG. 5. Accordingly, the multiple regression analysis is performed based on "comfort-discomfort". FIG. 11 is a view illustrating an example of multiple regression analysis in emotion estimating device 1 of the first embodiment. FIG. 11 illustrates data R3 obtained by performing the multiple regression analysis with scores around "delighted"–"depressed" as objective variables and 11 walking parameters of walking data 132 as explanatory variables. In the multiple regression analysis of FIG. 11, a multiple correlation coefficient R was 0.506218.

The score around the objective variables "delighted"–"depressed" is obtained by a combination of the score of the "delighted" emotion and the score of the "depressed" emotion. However, the score of the "depressed" emotion is evaluated on the 7-point scale as illustrated in FIG. 7, and the case of being the least depressed in life is set as "1 point", and the case of being the most depressed in life is set as "7 points". Therefore, when simply combined, the score in the case of being most depressed in life is not the lowest, and the score in the case of being most happy in life is not the highest. Accordingly, the score around "delighted"–"depressed" is defined by the following relational expression. The relational expression is "delighted"–"depressed" as an axis of score (objective variable)="delighted" emotion score+(8 points–"depressed" emotion score).

Specifically, in the case of the most delight in life, the score of the "delighted" emotion is 7 points, and the score of the "depressed" emotion is 1 point. Therefore, the objective variable=7 points+(8 points−1 points)=14 points. In the case where the user is the most depressed in life, the score of the "delighted" emotion is 1 point, and the score of the emotion of "depressed" is 7 points. Therefore, the objective variable=1 point+(8 points−7 points)=2 points. In the normal case, because the score of the "delighted" emotion is 4 points and the score of the "depressed" emotion is 4 points, the objective variable=4 points+(8 points−4 points)=8 points.

In data R3, coefficients of the explanatory variables with respect to the objective variable are illustrated. Among the explanatory variables indicated in the data R3, the absolute values of the coefficients of the three walking parameters of "stride", "pitch", and "walking speed" are as high as 3 or more. That is, the three walking parameters of "stride", "pitch", and "walking speed" have a large contribution to the target variable. Therefore, emotion estimating device 1 can estimate the emotion from walking data 134 in the range of "delighted"-"depressed" by adopting a multiple regression equation having three walking parameters of "stride", "pitch", and "walking speed" as explanatory variables as corresponding data 132.

Since the degree of contribution to the target variable is larger in the order of "walking speed", "stride", and "pitch", emotion estimating device 1 may estimate the emotion from the upper two walking parameters. Furthermore, emotion estimating device 1 may estimate the emotion from at least one walking parameter among three walking parameters of "stride", "pitch", and "walking speed". Furthermore, emotion estimating device 1 may estimate the emotion by adding a walking parameter other than the three walking parameters of "stride", "pitch", and "walking speed", and can enhance the estimation accuracy by increasing the walking parameter that estimates the emotion.

Returning to FIG. 4, emotion estimating device 1 can execute estimation processing II for estimating the emotion of subject P from newly received walking data 134 by previously obtaining corresponding data 132 in preparation processing I as described above. Emotion estimating device 1 determines whether new walking data 132 measured by measurement device 2 is received (step S106). When new walking data 132 is not received (NO in step S106), emotion estimating device 1 returns the processing to step S106 and waits for the input of new walking data 132.

When new walking data 132 is received (YES in step S106), emotion estimating device 1 estimates the emotion of subject P based on newly received walking data 132 and corresponding data 134 (step S107). Specifically, emotion estimating device 1 substitutes the values of the three walking parameters "stride", "pitch", and "walking speed" from newly received walking data 132 into the multiple regression equation in FIG. 11 to obtain the value of the objective variable, and estimates the emotion corresponding to the value. For example, emotion estimating device 1 estimates that the emotion of subject P is "delighted" when the value of the objective variable is close to 14 points, and estimates that the emotion of subject P is "depressed" when the value of the objective variable is close to 2 points.

Emotion estimating device 1 outputs information indicating the emotion of subject P estimated in step S107 from interface 14 (step S108). At this point, the information indicating the emotion includes not only simple information about characters or voices of "delighted", "depressed", and "irritated" but also information about icons, sounds, images, moving images, and the like corresponding to the emotions of "delighted", "depressed", and "irritated". Specifically, emotion estimating device 1 displays characters of "delighted", "depressed", and "irritated" on the display or outputs voices of "delighted", "depressed", and "irritated" from the speaker in response to the estimated emotion. In addition, as information indicating emotions, "delighted" may be scored and displayed as 100 points and "depressed" may be scored and displayed as 0 points, or emotions estimated may be plotted and displayed on a two-dimensional coordinate plane of the Russell's circumplex model. Furthermore, emotion estimating device 1 is not limited to a method capable of visually or audibly recognizing the information indicating the emotion, and may output the information by a method capable of recognizing the information by smell, touch, or the like.

Second Embodiment

In emotion estimating system 100 of the first embodiment, the estimation of the emotion of subject P from walking data 132 has been described. However, when it is known that there is a certain correspondence relationship between the emotion and the gait, there is a possibility that the emotion can be changed by changing the gait. Therefore, in an emotion estimating system according to a second embodiment, a configuration in which walking advice that changes the emotion estimated from the walking data to a different emotion is performed will be described. The emotion estimating system of the second embodiment has the same hardware configuration as emotion estimating system 100 of the first embodiment, and includes the hardware configuration of emotion estimating device 1. Accordingly, the hardware configuration of the emotion estimating system of the second embodiment will not be described in detail.

Figure 12:
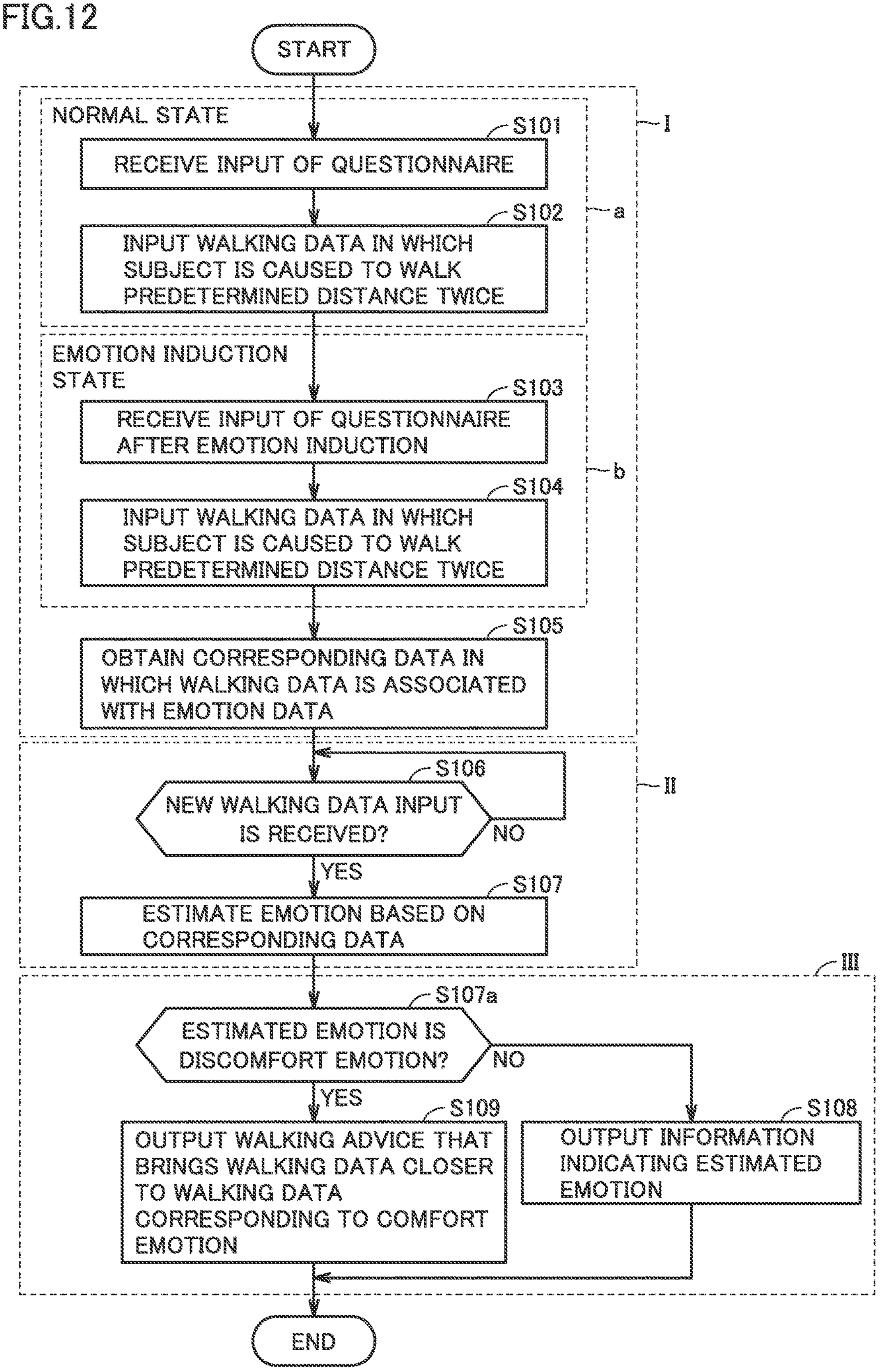
FIG. 12 is a flowchart for describing emotion estimation processing executed by an emotion estimating device according to a second embodiment.

FIG. 12 is a flowchart for describing emotion estimation processing executed by an emotion estimating device 1 of the second embodiment. Because preparation processing I and estimation processing II in FIG. 12 are the same processing as preparation processing I and estimation processing II in FIG. 4, detailed description will not be repeated. In the flowchart of FIG. 12, after estimation processing II, recommendation processing III for giving walking advice that changes the estimated emotion to a different emotion is performed.

Emotion estimating device 1 determines whether the emotion of subject P estimated in step S107 is an emotion classified as discomfort in the Russell's circumplex model illustrated in FIG. 5 (step S107*a*). Specifically, in the case where the value of the objective variable obtained from the multiple regression equation in FIG. 11 is smaller than 8 points, emotion estimating device 1 estimates that the emotion of subject P is "depressed" and determines that the emotion is the discomfort emotion. Conversely, in the case where the value of the objective variable obtained from the multiple regression equation in FIG. 11 is greater than or equal to 8 points, emotion estimating device 1 estimates the emotion of subject P as "delighted" and determines that the emotion is the comfort emotion. When the value of the objective variable is 8 points, emotion estimating device 1 may determine that the emotion of subject P is in the normal state.

When it is determined that the emotion of subject P is the comfort emotion (NO in step S107*a*), emotion estimating device 1 outputs information indicating the emotion of subject P estimated in step S107 from interface 14 (step S108).

On the other hand, when the emotion of subject P is determined to be the discomfort emotion (YES in step S107*a*), emotion estimating device 1 obtains walking data 132 associated with the comfort emotion from corresponding data 134, and outputs the walking advice that brings walking data 132 estimated to be the discomfort emotion closer to walking data 132 associated with the comfort emotion from interface 14 (step S109). Specifically, when the emotion of subject P is estimated as "depressed" and determined as the discomfort emotion, emotion estimating device 1 obtains the value of the walking parameter in which the value of the objective variable estimated as the "delighted" emotion is 14 points from the multiple regression equation in FIG. 11. Furthermore, emotion estimating device 1 displays the walking advice such as "please walk a little faster" on the display in order to bring the walking parameter of subject P closer to the obtained value of the walking parameter.

When subject P improves walking by receiving the walking advice, the emotion of subject P may be changed from the discomfort emotion to the comfort emotion. In the flowchart of FIG. 12, recommendation processing III for giving the walking advice in order to replace the discomfort emotion (first emotion) with the comfort emotion (second emotion) has been described. However, of course the walking advice can be given in order to replace the comfort emotion (first emotion) with the discomfort emotion (second emotion). In addition, the walking advice may be given with the first emotion as calm and the second emotion as awakening, or the walking advice may be given with the first emotion as awakening and the second emotion as calm.

Third Embodiment

In emotion estimating system 100 of the first embodiment, it has been described that emotion estimating device 1 needs to previously obtain the corresponding data in which the plurality of walking parameters included in the walking data are associated with the emotion data in order to estimate the emotion of subject P from the walking data. However, in the association processing based on the example described in the first embodiment, it has been found that at least one walking parameter among the three walking parameters of "stride", "pitch", and "walking speed" has a high degree of contribution to the emotion of subject P. Accordingly, in a third embodiment, an emotion estimating device that scores the emotion of subject P from these walking parameters to easily estimate the emotion and an emotion estimating system including the emotion estimating device will be described.

Figure 13:
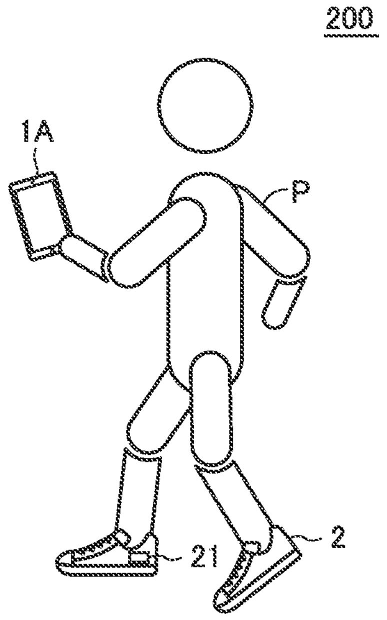
FIG. 13 is a schematic diagram illustrating a configuration of an emotion estimating system including an emotion estimating device according to a third embodiment.

FIG. 13 is a schematic diagram illustrating a configuration of an emotion estimating system 200 including an emotion estimating device 1A of the third embodiment. Emotion estimating system 200 includes emotion estimating device 1A that scores the emotion of subject P from the walking data around "delighted"–"depressed" of the Russell's circumplex model in FIG. 5, and a measurement device 2 that measures the walking data of subject P. The notation "delighted" of the Russell's circumplex model will be replaced with "lively" in the following description.

Emotion estimating device 1A needs to perform comparison with population data previously prepared in order to score the emotion of subject P from the walking data. In the present disclosure, an example of scoring the emotion using generalized population data including the walking data of subject with various attributes (for example, gender, age, and race) will be described. However, the population data appointed by emotion estimating device 1A may be population data including walking data collected for each attribute (for example, gender, age, and race), population data including walking data collected for each individual (for example, cumulative over the last 10 days), or the like. Furthermore, in the present disclosure, it is described that the population data is stored in emotion estimating device 1A, but the population data may be stored in a place other than emotion estimating device 1A such as a cloud.

In emotion estimating system 200 of FIG. 13, an example in which measurement device 2 is the smart shoe is illustrated. In FIG. 13, sensor module 21 is incorporated in the smart shoe that is measurement device 2, and the walking data of subject P is measured by sensor module 21. Because sensor module 21 has been described in the first embodiment, the detailed description of sensor module 21 will not be repeated.

Figure 14:
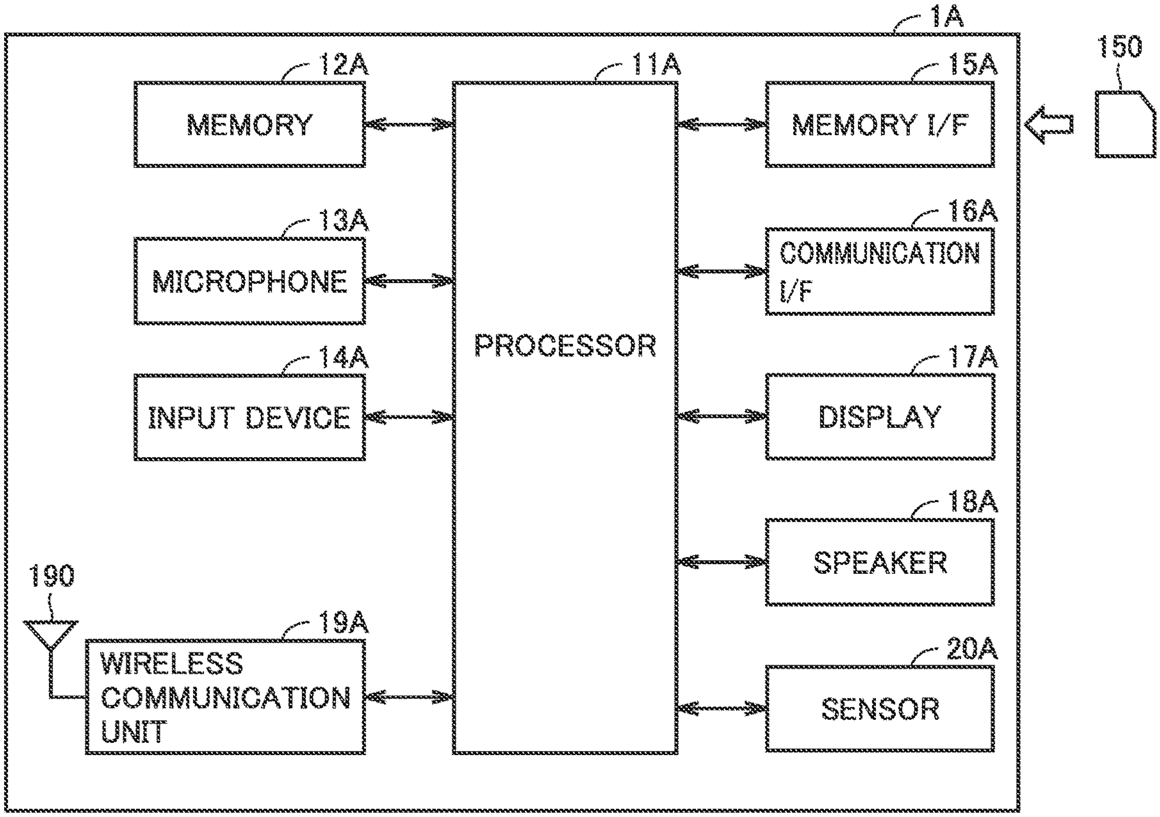
FIG. 14 is a block diagram illustrating a configuration of the emotion estimating device of the third embodiment.

FIG. 14 is a block diagram illustrating a configuration of emotion estimating device 1A of the third embodiment. For example, emotion estimating device 1A is a portable terminal of subject P such as a smartphone or a tablet terminal. Emotion estimating device 1A includes a processor 11A, a memory 12A, a microphone 13A, an input device 14A, a memory interface (UF) 15A, a communication interface (UF) 16A, a display 17A, a speaker 18A, a wireless communication unit 19A, and a sensor 20A.

Processor 11A is typically a computer such as a CPU or an MPU. Processor 11A functions as a control unit that controls operation of each unit of emotion estimating device 1 by reading and executing a program stored in memory 12A. Processor 11A executes the program to implement scoring processing of the emotion of subject P in emotion estimating device 1.

Memory 12A is implemented by a RAM, a ROM, a flash memory, and the like. Memory 12A stores the program executed by processor 11A, data used by processor 11A, or the like. Microphone 13A receives a voice input to emotion estimating device 1A and provides a voice signal corresponding to the voice input to processor 11A.

Input device 14A receives the operation input to emotion estimating device 1A. Typically, input device 14A is implemented by a touch panel. The touch panel is provided on display 17A having a function as a display unit, and for example, is a capacitive type. The touch panel detects a touch operation on the touch panel by an external object every predetermined time, and inputs touch coordinates to processor 11A. However, input device 14A may include a button or the like.

Memory interface 15A reads data from external storage medium 150. Processor 11A reads the data stored in storage medium 150 through memory interface 15A, and stores the data in memory 12A. Processor 11A reads the data from memory 12A and stores the data in external storage medium 150 through memory interface 15A.

Storage medium 150 includes a medium that stores a program in a nonvolatile manner, such as a compact disc (CD), a digital versatile disk (DVD), a Blu-ray (registered trademark) disc (BD), a universal serial bus (USB) memory, or a secure digital (SD) memory card.

Communication interface (UF) 16A is a communication interface that exchanges various data between emotion estimating device 1A and measurement device 2, and is implemented by an adapter, a connector, or the like. For example, a wireless communication method using Bluetooth (registered trademark) low energy (BLE), or a wireless LAN is adopted as a communication method.

Speaker 18A converts the voice signal provided from processor 11A into the voice and outputs the voice to the outside of emotion estimating device 1A.

Wireless communication unit 19A is connected to a mobile communication network through a communication antenna 190 and transmits and receives the signal for wireless communication. Thus, emotion estimating device 1A can communicate with another communication device through the mobile communication network such as long term evolution (LTE) or 5G.

Sensor 20A is an acceleration sensor, and can measure the motion of subject P carrying emotion estimating device 1A. Accordingly, sensor 20A can detect an immobility time during which subject P is sitting or sleeping.

[Mind Score Calculation Processing]

Figure 15:
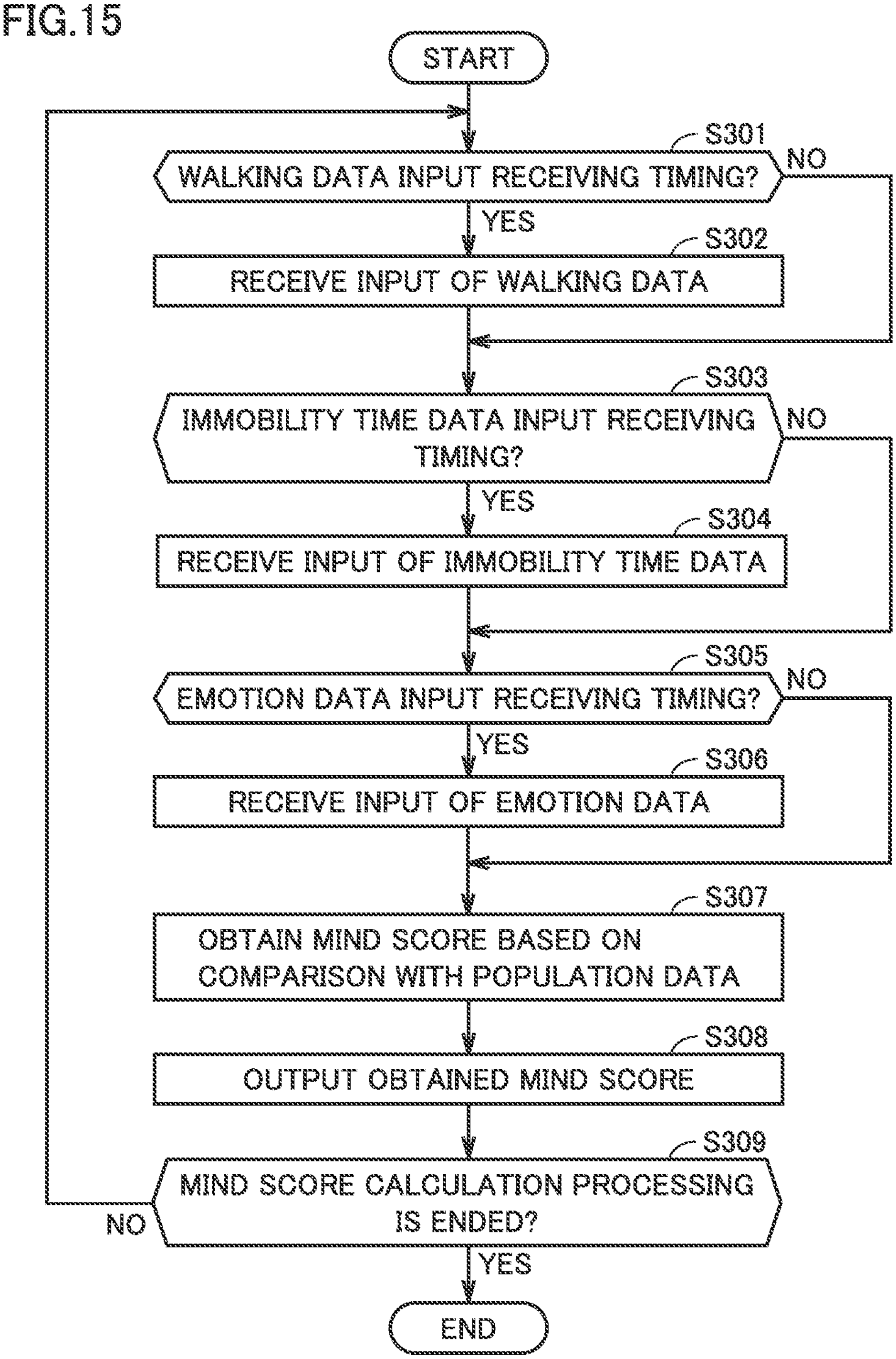
FIG. 15 is a flowchart for describing processing in which the emotion estimating device of the third embodiment obtains a mind score.

Processing in which emotion estimating device 1A obtains the mind score by scoring the emotion of subject P around "lively"–"depressed" of the Russell's circumplex model will be described below. At this point, the mind score is an evaluation value obtained by scoring the emotion of subject P with "lively" as 100 points and "depressed" as 1 point. FIG. 15 is a flowchart for describing processing in which emotion estimating device 1A of the third embodiment obtains the mind score.

Emotion estimating device 1A receives the input of the walking data measured by measurement device 2 every predetermined period (for example, every minute). The case where emotion estimating device 1A is always connected to measurement device 2 will be described below, but emotion estimating device 1A may not be always connected to measurement device 2. When emotion estimating device 1A is not always connected to measurement device 2, emotion estimating device 1A receives the input of the walking data at timing when emotion estimating device 1A is connected to measurement device 2. For example, in the case where emotion estimating device 1A is a smartphone and measurement device 2 is sensor module 21 of the smart shoe, the smartphone receives the input of the walking data at timing when subject P wears the smart shoe and starts communication between the smartphone and sensor module 21. When the smartphone and sensor module 21 are in a communicable state, thereafter, the smartphone may receive the input of the walking data from sensor module 21 every predetermined period (for example, every minute).

First, emotion estimating device 1A determines whether it is timing to accept the input of the walking data (step S301). When it is determined that it is the timing to receive the input of the walking data (YES in step S301), emotion estimating device 1A receives the input of the walking data measured by measurement device 2 (step S302). The walking data received by emotion estimating device 1A includes parameters of the walking speed, the stride, and the ground contact angle (the toe upward angle at time of landing or the heel upward angle at time of leaving).

Emotion estimating device 1A only needs to receive the walking data including at least one parameter of the walking speed, the stride, and the pitch in order to obtain the mind score. Furthermore, the following description will be given assuming that the walking data is data measured by measurement device 2, but walking parameters such as the walking speed, the stride, and the pitch may be measured by sensor 20A (the acceleration sensor of the smartphone) of emotion estimating device 1A or may be measured by another wearable device.

When it is determined that it is not the timing to receive the input of the walking data (NO in step S301), emotion estimating device 1A skips the processing of step S302. Emotion estimating device 1A receives the input of immobility time data every predetermined period (for example, every minute). Emotion estimating device 1A determines whether it is the timing to receive the input of the immobility time data (step S303). When it is determined that it is the timing to receive the input of the immobility time data (YES in step S303), emotion estimating device 1A receives the input of the immobility time data (step S304).

At this point, the immobility time data is the time during which subject P is not walking, for example, the time during which subject P is sitting or sleeping. The immobility time data is measured by sensor 20A (the acceleration sensor of the smartphone) of emotion estimating device 1A. Alternatively, the immobility time data may be calculated from the walking parameter obtained from the smart shoes as measurement device 2.

Emotion estimating device 1A can also score the emotion of subject P other than at the time of walking by correcting the mind score using the immobility time data in addition to the walking data, and can obtain the mind score. Specifically, emotion estimating device 1A subtracts the point from the mind score according to the immobility time data. This is based on the result of a study in which the relationship between the sitting time and the mental health was verified (*Yuko* KAI and four others, "Relationship between Sitting Behavior and Mental Health in Japanese Workers", Physical Fitness Research, BULLETIN OF THE PHYSICAL FITNESS RESEARCH INSTITUTE, No. 114, pp. 1 to 10, Apr., 2016) that the mental health was degraded when the sitting time was long. Consequently, emotion estimating device 1A can score the emotion of subject P other than walking by subtracting the score corresponding to the immobility time during which subject P is not walking from the mind score obtained at the time of walking.

When it is determined that it is not the timing to receive the input of the immobility time data (NO in step S303), emotion estimating device 1A skips the processing of step S304. Subsequently, emotion estimating device 1A receives the input of the emotion data at predetermined timing (for example, once every morning). Emotion estimating device 1A determines whether it is the timing to accept the input of the emotion data (step S305). When it is determined that it is the timing to receive the input of the emotion time data (YES in step S305), emotion estimating device 1A receives the input of the emotion data (step S306). At this point, the emotion data is a subjective evaluation value of subject P obtained by subject P answering the questionnaire displayed on display 17A of emotion estimating device 1A.

Figure 16:
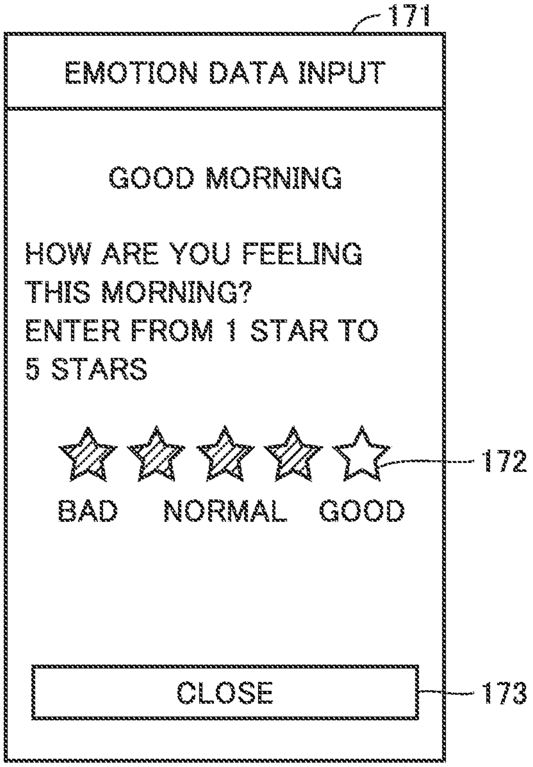
FIG. 16 is a view illustrating an example of an input screen that inputs emotion data in the emotion estimating device of the third embodiment.

FIG. 16 is a view illustrating an example of an input screen that inputs emotion data in emotion estimating device 1A of the third embodiment. On input screen 171 displayed on display 17A, "Good morning", "How are you feeling this morning?", and "Enter from 1 star to 5 stars" are displayed, and a star input screen 172 is displayed. Subject P inputs 1 star when subject P feels bad according to the mood of this morning, and inputs 5 stars when subject P feels good using input device 14A (for example, the touch panel). Thereafter, subject P presses a "close" button 173 to end the input of the emotion data. The input of the emotion data may be a numerical value such as 1% to 100% instead of five stages.

Emotion estimating device 1A can improve the accuracy of the mind score by correcting the mind score using the emotion data in addition to the walking data. The mind score obtained from the walking data fluctuates greatly according to the mood of subject P. Accordingly, emotion estimating device 1A can adjust the mind score according to the mood of the day by inputting the emotion data once every morning, and the accuracy of the mind score is improved. In particular, the input of the emotion data once every morning means initial value adjustment when the activity from the state of sleeping for a long time is started to start scoring of the emotion by the walking data. However, the timing of inputting the emotion data is not limited to once every morning, but the emotion data may be input every several hours. The number of times of inputting the emotion data is desirably set to such a number that subject P does not feel bothersome to the input operation. Furthermore, the content of the emotion data is not limited to the mood of subject P this morning, but may be subjective evaluation values of subject P such as the current mood, physical fatigue, and sleep quality according to the questionnaire displayed on input screen 171.

Returning to FIG. 15, when it is determined that it is not the timing to receive the input of the emotion time data (NO in step S305), emotion estimating device 1A skips the processing in step S306. Subsequently, emotion estimating device 1A obtains the mind score based on the comparison between the walking parameter (for example, the walking speed, the stride, and the ground contact angle) and the population data (step S307).

Figure 17:
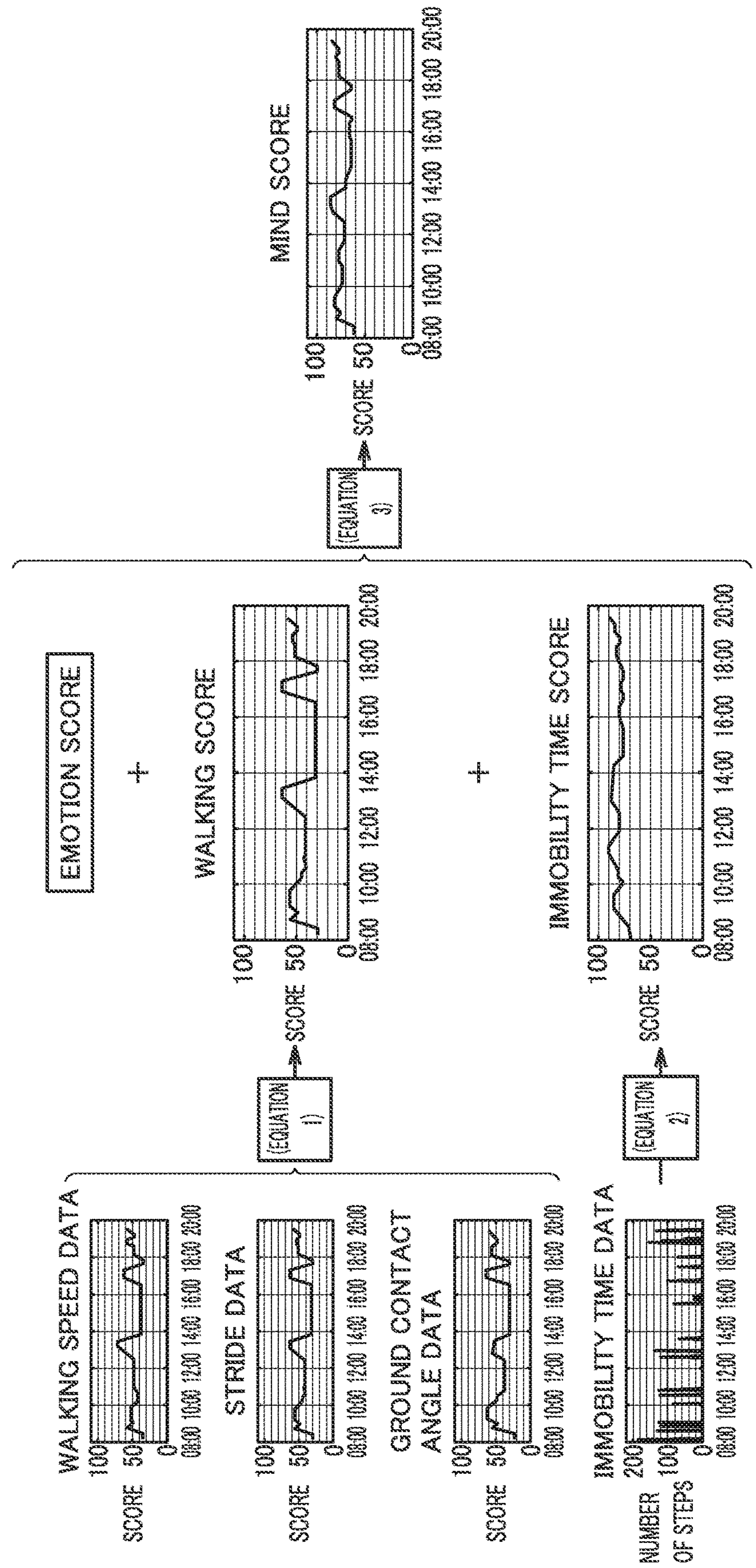
FIG. 17 is a view for describing an example of an operation that obtains the mind score in the emotion estimating device of the third embodiment.

Specifically, how to obtain the mind score will be described. FIG. 17 is a view for describing an example of an operation that obtains the mind score in emotion estimating device 1A of the third embodiment. In FIG. 17, emotion estimating device 1A calculates the mind score from the three walking parameters (for example, the walking speed, the stride, and the ground contact angle) input in step S301. Emotion estimating device 1A can calculate the mind score every predetermined period (for example, every minute) by receiving the input of the walking data from measurement device 2 every predetermined period.

The three walking parameters of the walking speed, the stride, and the ground contact angle can be estimated to be more "lively" emotion as the value is larger. Accordingly, emotion estimating device 1A calculates the walking score based on the value of each walking parameter and the population data according to the following Equation 1. Equation 1 is an example, and the walking score may be calculated by another equation.

$$\text{Walking score}=A^*\text{walking speed score}+B^*\text{stride score}+C^*\text{ground contact angle score} \quad \text{(Equation 1)}$$

At this point, the walking speed score, the stride score, and the ground contact angle score are calculated as follows.

$$\text{Walking speed score}=D1+E1^*(\text{walking speed}-\text{average value of population data of walking speed})/\text{standard deviation of population data of walking speed.}$$

$$\text{Stride score}=D2+E2^*(\text{average value of stride}-\text{stride population data})/\text{standard deviation of population data of stride.}$$

$$\text{Ground contact angle score}=D3+E3^*(\text{ground contact angle}-\text{average value of population data of ground contact angles})/\text{standard deviation of population data of ground contact angles.}$$

A to C are weighting coefficients for each score. The values of A to C can be set, for example, in a range of 0.1 to 0.9, and the condition that A+B+C=1 is satisfied. In addition, D1 to D3 are initial values of each score, and for example, can be set to the value in the range of 40 to 80, and may be all the same values or different values. E1 to E3 are addition coefficients of each score, and for example, can be set to the value in the range of 5 to 20, and may be all the same value or different values. The walking score is the value from 1 point to 100 points, and is 100 points when the walking score is greater than or equal to 100 points.

It can be estimated that the longer the immobility time included in the immobility time data, the closer to the "depressed" emotion. Accordingly, emotion estimating device 1A calculates the immobility time score according to the following Equation 2. Equation 2 is an example, and the immobility time score may be calculated by another equation.

$$\text{Immobility time score}=F-G(\text{immobility time}-60\ \text{min}) \quad \text{(Equation 2)}$$

F is an initial value of the immobility time score, and for example, can be set to the value in the range of 40 to 80. G is a subtraction coefficient of the immobility time score, and for example, can be set to the value in the range of 1 to 5. The immobility score is the value from 1 point to 100 points, and is 1 point when the immobility score is less than or equal to 1 point. In addition, in a time period in which the walking data can be acquired, the immobility time score may be increased by 1 point every minute.

For example, the emotion score is scored as −2 points for 1 star, −1 points for 2 stars, 0 points for 3 stars, 1 point for 4 stars, and 2 points for 5 stars based on the emotion data input on input screen 171 in FIG. 16.

As illustrated in FIG. 17, emotion estimating device 1A calculates the mind score by summing the walking score calculated by Equation 1, the immobility time score calculated by Equation 2, and the emotion score. Specifically, emotion estimating device 1A calculates the mind score based on Equation 3. Equation 3 is an example, and the mind score may be calculated by another equation.

$$\text{Mind score}=((\text{walking score}+\text{immobility time score})/2)+\text{emotion score}^*10 \quad \text{(Equation 3)}$$

For example, emotion estimating device 1A calculates the mind score using the most recently calculated walking score for a period in which the walking data cannot be obtained from measurement device 2 such that the 24 hour mind score can be calculated. Furthermore, emotion estimating device 1A can calculate the mind score with the value of the immobilization time score+the emotion score*10 such that the mind score can be calculated even when the most recently calculated walking score is unavailable (for example, in the case where subject P does not walk throughout the day).

Figure 18:
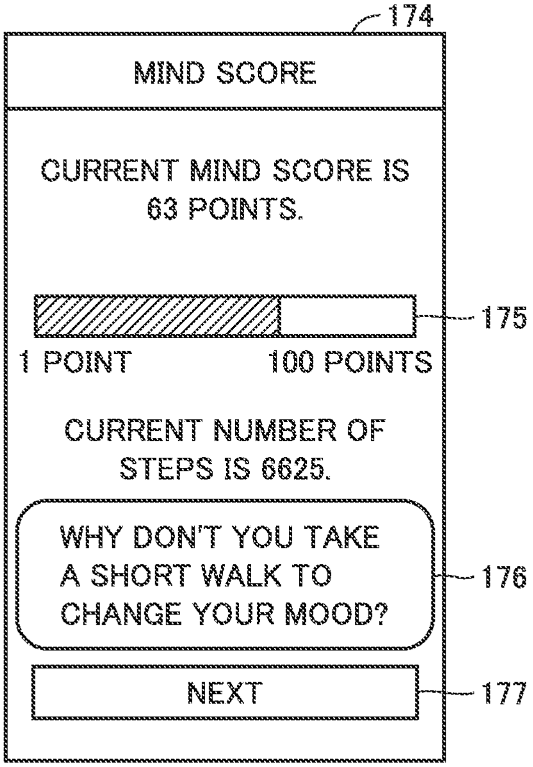
FIG. 18 is a view illustrating an example of an output screen that outputs the mind score in the emotion estimating device of the third embodiment.

Returning to FIG. 15, emotion estimating device 1A outputs the mind score obtained in step S307 (step S308). Specifically, emotion estimating device 1A displays the obtained mind score on display 17A. FIG. 18 is a view illustrating an example of an output screen 174 that outputs the mind score in the emotion estimating device 1A of the third embodiment. On output screen 174 displayed on display 17A, the mind score is displayed as a bar graph 175 together with the numerical value of the current mind score. The mind score displayed on display 17A may be the mind score updated every 1 minute, the mind score having an accumulated average value for a day, or a value obtained by averaging the mind scores in the active time period.

In addition to the mind score, walking advice 176 corresponding to the current number of steps and the mind score is also output on output screen 174. In walking advice 176, because the mind score is lowered, "why don't you take a short walk to change your mood?" is given to urge subject P to walk. Although the walking score, the immobility time score, and the emotion score are not displayed on output screen 174, the walking score, the immobility time score, and the emotion score may be displayed.

Figure 19:
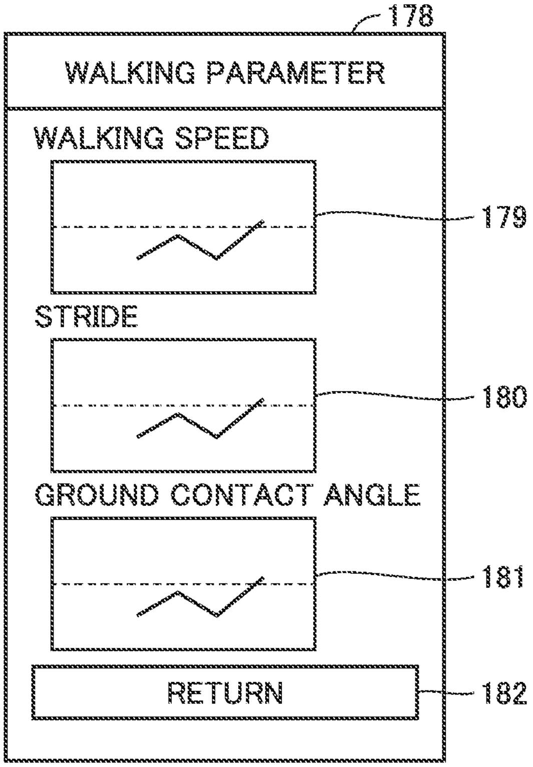
FIG. 19 is a view illustrating an example of the output screen that outputs the walking parameter in the emotion estimating device of the third embodiment.

Emotion estimating device 1A may output the temporal change of each walking parameter in addition to the output of the mind score. Specifically, when a "next" button 177 on output screen 174 in FIG. 18 is pressed, the time-series change in each walking parameter is output. FIG. 19 is a view illustrating an example of an output screen 178 that outputs the walking parameter in emotion estimating device 1A of the third embodiment. A time-series graph 179 of the walking speed, a time-series graph 180 of the stride, and a time-series graph 181 of the ground contact angle are displayed on an output screen 178. Emotion estimating device 1A may be able to display only the time-series graph of the walking parameter selected by subject P on output screen 178. When a "return" button 182 on output screen 178 in FIG. 19 is pressed, display 17A returns to output screen 174 in FIG. 18.

Returning to FIG. 15, after outputting the mind score in step S308, emotion estimating device 1A receives the input as to whether to end the mind score calculation processing (step S309). When the input for ending the mind score calculation processing is not received (NO in step S309), emotion estimating device 1A returns the processing to step S301 and continues the mind score calculation processing. On the other hand, when the input for ending the mind score calculation processing is received (YES in step S309), emotion estimating device 1A ends the mind score calculation processing.

Figure 20:
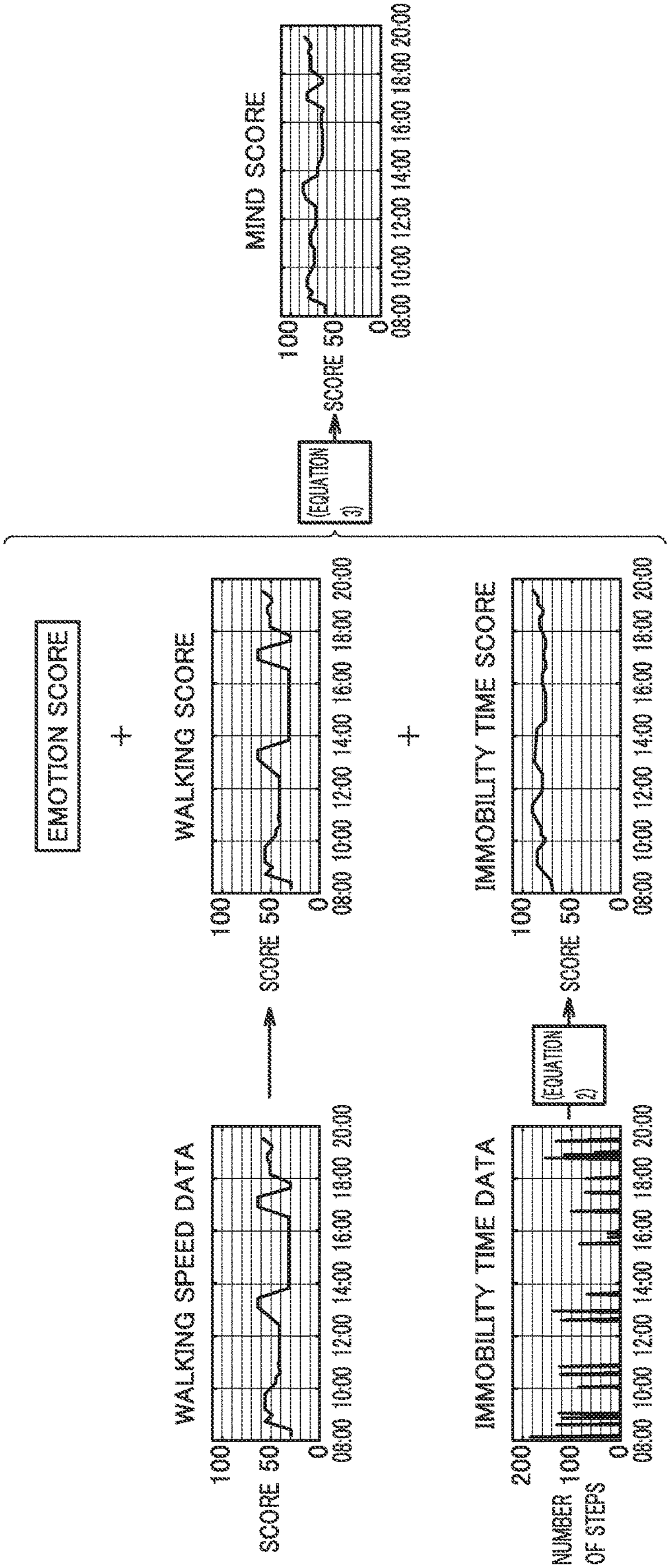
FIG. 20 is a view for describing an example of another operation that obtains the mind score in the emotion estimating device of the third embodiment.

In the method for obtaining the mind score described with reference to FIG. 17, the mind score is calculated from the three walking parameters (for example, the walking speed, the stride, and the ground contact angle) input in step S301. However, emotion estimating device 1A can calculate the mind score from at least one parameter of the walking speed, the stride, and the pitch. FIG. 20 is a view for describing an example of another operation that obtains the mind score in emotion estimating device 1A of the third embodiment. In FIG. 20, emotion estimating device 1A calculates the mind score from one walking parameter (for example, the walking speed) input in step S301.

In FIG. 20, emotion estimating device 1A calculates the walking speed score as the walking score. Emotion estimating device 1A calculates the mind score by summing the walking score (=walking speed score), the immobility time score calculated by Equation 2, and the emotion score. Specifically, emotion estimating device 1A calculates the mind score based on Equation 3.

Furthermore, in the third embodiment, it has been described that emotion estimating device 1A scores the emotion of subject P from the walking data with axes of "lively"-"depressed" of the Russell's circumplex model, but the axes may be further expanded to the range of "lively"–"depressed". For example, emotion estimating device 1A scores the emotion of subject P by setting the mind score to 100 points for "lively", 1 point for "depressed", and −20 points for "gloom". The "gloom" state is considered to be the state in which the mind is further lowered than the "depressed" state. There is also a research result in the literature (Tsutomu Murata, and 4 others, "Characteristics of walking of elderly person having depression tendency", Japanese Journal of Health Promotion and Physical Therapy, Vol. 7, No. 3: 127-131, 2017) that "As characteristics of the gait of an elderly person who tends to be depressed, a decrease in stride and stride involved in a decrease in walking speed and an increase in standing time and both leg support time were recognized.", and it is considered that the score is even lower from the mind score when "depressed".

[Modification]

The present disclosure is not limited to the above-described embodiments, but various modifications and applications are possible. In particular, the analysis and method for associating walking data 132 and emotion data 133 described above are merely examples. For example, by scoring not only the axis of "comfort-discomfort" but also the axis of "awakening-calming" of the Russell's annular model in FIG. 5, various emotions classified on the two-dimensional coordinate plane of the Russell's annular model can be estimated from walking data 132.

In the case where measurement device 2 is the smart shoe, the walking parameters that can be measured as the walking data include the stride, the pitch, the walking speed, the time required for one step, the stance phase period, the swing phase period, the toe upward angle at time of landing, the heel upward angle at time of leaving, the pronation, the maximum foot upward height, and the maximum value of acceleration in the vertical direction at the time of landing. Consequently, walking data 132 that can receive the input by emotion estimating device 1 can include at least three parameters of the stride, the pitch, the walking speed, the time required for one step, the stance phase period, the swing phase period, the toe upward angle at time of landing, the heel upward angle at time of leaving, the pronation, the maximum foot upward height, and the maximum value of acceleration in the vertical direction at the time of landing. The walking parameter described above is an example of the walking parameter that can be measured in the smart shoes, and another walking parameter may be obtained by calculation, or another sensor may be provided such that another walking parameter can be measured.

In the case where measurement device 2 is the smartphone, depending on the model, the walking parameter that can be measured as the walking data may not include the toe upward angle at time of landing, the heel upward angle at time of leaving, the pronation, and the maximum foot upward height. In this case, walking data 132 that can receive the input by emotion estimating device 1 can include at least two parameters of the stride, the pitch, the walking speed, the time required for one step, the stance phase period, and the swing phase period. Even in the case where measurement device 2 is the smartphone, the toe upward angle at time of landing, the heel upward angle at time of leaving, the pronation, the maximum foot upward height, and the walking parameter of the maximum value of the acceleration in the vertical direction at the time of landing can be acquired from information from another three-dimensional posture recognition camera or the like.

In the above-described embodiment, walking data 132 is measured by measurement device 2 in the state where the emotion induction is performed to impart the specific emotion to subject P. However, the method for causing subject P to have the specific emotion is not limited to the emotion induction, and subject P may be made aware of the specific emotion to cause subject P to have the specific emotion. In addition, subject P may be caused to walk at the timing when subject P has the specific emotion, and walking data 132 may be measured by measurement device 2.

[Aspects]

(1) An emotion estimating device according to the present disclosure is an emotion estimating device that estimates an emotion of a subject, the emotion estimating device including: an interface that receives input of walking data of the subject measured by a measurement device and emotion data obtained by quantifying the emotion of the subject; a storage that stores the walking data and the emotion data received by the interface; and a computer that obtains corresponding data in which a plurality of walking parameters included in the walking data stored in the storage are associated with the emotion data, in which when the input of the walking data is newly received in the interface, the computer estimates the emotion of the subject from the plurality of walking parameters included in the newly received walking data based on the corresponding data, and outputs information indicating the estimated emotion of the subject from the interface.

Thus, the emotion estimating device of the present disclosure estimates the emotion of the subject from the plurality of walking parameters included in the newly received walking data based on the corresponding data, so that the emotion estimating device can estimate the emotion of the subject based on the walking data obtained from daily activities.

(2) The emotion estimating device according to (1), in which the walking data includes at least one parameter of the plurality of walking parameters including a stride, a pitch, and a walking speed.

(3) The emotion estimating device according to (1), in which the walking data includes at least two parameters of a stride, a pitch, a walking speed, a time required for one step, a stance phase period, a swing phase period, and a toe upward angle at time of landing.

(4) The emotion estimating device according to (1), in which the walking data includes at least three parameters of a stride, a pitch, a walking speed, a time required for one step, a stance phase period, a swing phase period, a toe upward angle at time of landing, a heel upward angle at time of leaving, a pronation, a maximum foot upward height, and a landing impact.

(5) The emotion estimating device according to any one of (1) to (4), in which when the emotion of the subject newly estimated from the walking data is a first emotion, the computer obtains the walking data associated with a second emotion different from the first emotion from the corresponding data, and outputs a walking advice from the interface in order to bring the walking data estimated as the first emotion closer to the walking data associated with the second emotion.

(6) The emotion estimating device according to (5), in which the first emotion is an emotion classified as discomfort, and the second emotion is an emotion classified as comfort.

(7) An emotion estimating system according to the present disclosure includes a measurement device that measures the walking data of the subject, and the emotion estimating device according to any one of (1) to (6).

(8) An emotion estimating method according to the present disclosure is an emotion estimating method for estimating an emotion of a subject, the emotion estimating method including: receiving input of walking data of the subject measured by a measurement device and emotion data obtained by quantifying the emotion of the subject; storing the input walking data and the input emotion data in a storage; obtaining corresponding data in which a plurality of walking parameters included in the walking data stored in the storage are associated with the emotion data; when the input of the walking data is newly received, estimating the emotion of the subject from the plurality of walking parameters included in the newly received walking data based on the corresponding data; and outputting information indicating the estimated emotion of the subject.

(9) The emotion estimating method according to (8), further including, when the emotion of the subject newly estimated from the walking data is a first emotion, obtaining the walking data associated with a second emotion different from the first emotion from the corresponding data, and outputting walking advice for bringing the walking data estimated as the first emotion closer to the walking data associated with the second emotion.

(10) Another emotion estimating device according to the present disclosure is an emotion estimating device that scores an emotion based on an axis of a Russell's circumplex model to estimate an emotion of a subject, the emotion estimating device including: an input circuitry that receives walking data of the subject measured by a measurement device; a storage that stores population data of each parameter for a plurality of walking parameters included in the walking data; an computer that obtains a mind score that scores the emotion of the subject based on comparison between at least one parameter of a stride, a pitch, and a walking speed among the plurality of walking parameters included in the walking data received by the input circuitry and the population data stored in the storage; and an output circuitry that outputs the mind score obtained by the computer.

(11) The emotion estimating device according to (10), in which the computer obtains the mind score based on comparison between the population data stored in the storage and each parameter of a toe upward angle at time of landing or a heel upward angle at time of leaving in addition to the stride and the walking speed among the plurality of walking parameters.

(12) The emotion estimating device according to (10) or (11), in which the input circuitry receives input of immobility time data in which the subject is not walking, and the computer corrects the mind score with the immobility time data received by the input circuitry.

(13) The emotion estimating device according to any one of (10) to (12), in which the input circuitry receives input of emotion data obtained by quantifying the emotion of the subject, and the computer corrects the mind score with the emotion data received by the input circuitry.

(14) The emotion estimating device according to any one of (10) to (13), in which the computer obtains the mind score using a value obtained by dividing a difference value between the walking parameter and an average value of the population data by a standard deviation of the population data.

(15) The emotion estimating device according to any one of (10) to (14), in which the computer outputs walking advice according to the obtained mind score from the output circuitry.

(16) Another emotion estimating system according to the present disclosure includes a measurement device that measures the walking data of the subject, and the emotion estimating device according to any one of (10) to (15).

(17) Another emotion estimating method according to the present disclosure is an emotion estimating method for estimating an emotion of a subject by scoring an emotion based on an axis of a Russell's circumplex model, the emotion estimating method including: receiving walking data of the subject measured by a measurement device; obtaining a mind score that scores the emotion of the subject based on comparison between at least one parameter of a stride, a pitch, and a walking speed among a plurality of walking parameters included in the received walking data and population data stored in a storage; and outputting the obtained mind score.

Although the embodiments of the present invention have been described, it should be considered that the disclosed embodiment is an example in all respects and not restrictive. The scope of the present invention is indicated by the claims, and it is intended that all modifications within the meaning and scope of the claims are included in the present invention.

What is claimed is:

1. An emotion estimating device that estimates an emotion of a subject, the emotion estimating device comprising:

an interface configured to receive input of walking data of the subject measured by a measurement device and emotion data obtained by quantifying the emotion of the subject;

a storage configured to store the walking data and the emotion data received by the interface; and a computer configured to obtain corresponding data in which a plurality of walking parameters included in the walking data stored in the storage are associated with the emotion data, wherein the computer is configured to apply a main component analysis to the plurality of walking parameters to obtain a main component by synthesizing and dimensionally compressing variables that represent a variation of the walking data and the emotion data of the subject, the main component indicating a tendency exerted on the plurality of walking parameters for the emotion of the subject, the computer is further configured to obtain the corresponding data through the main component analysis of the plurality of walking parameters and a multiple regression analysis with a score of the emotion data as an objective variable and the plurality of walking parameters included in the walking data as explanatory variables, when the input of the walking data is newly received in the interface, the computer is configured to estimate the emotion of the subject from the plurality of walking parameters included in the newly received walking data based on the corresponding data, and output information indicating the estimated emotion of the subject from the interface, and when the emotion of the subject newly estimated from the walking data is a first emotion, the computer is configured to:

identify, from the corresponding data, a target set of walking parameters associated with a second emotion different from the first emotion;

determine a difference between the plurality of walking parameters included in the newly received walking data and the target set of walking parameters; and output a walking advice from the interface based on the determined difference in order to bring the walking data estimated as the first emotion closer to the walking data associated with the second emotion.

2. The emotion estimating device according to claim 1, wherein the walking data includes at least one parameter of the plurality of walking parameters including a stride, a pitch, and a walking speed.

3. The emotion estimating device according to claim 1, wherein the walking data includes at least two parameters of a stride, a pitch, a walking speed, a time required for one step, a stance phase period, a swing phase period, and a toe upward angle at time of landing.

4. The emotion estimating device according to claim 1, wherein the walking data includes at least three parameters of a stride, a pitch, a walking speed, a time required for one step, a stance phase period, a swing phase period, a toe upward angle at time of landing, a heel upward angle at time of leaving, a pronation, a maximum foot upward height, and a landing impact.

5. The emotion estimating device according to claim 1, wherein the first emotion is an emotion classified as discomfort, and the second emotion is an emotion classified as comfort.

6. An emotion estimating system comprising:

a measurement device configured to measure the walking data of the subject; and the emotion estimating device according to claim 1.

7. An emotion estimating system comprising:

a measurement device configured to measure the walking data of the subject; and the emotion estimating device according to claim 1.

8. An emotion estimating method for estimating an emotion of a subject, the emotion estimating method comprising:

receiving input of walking data of the subject measured by a measurement device and emotion data obtained by quantifying the emotion of the subject;

storing the input walking data and the input emotion data in a storage;

applying a main component analysis to a plurality of walking parameters included in the walking data stored in the storage to obtain a main component by synthesizing and dimensionally compressing variables that represent a variation of the walking data and the emotion data of the subject, the main component indicating a tendency exerted on the plurality of walking parameters for the emotion of the subject;

obtaining corresponding data in which the plurality of walking parameters are associated with the emotion data, the corresponding data being obtained through the main component analysis of the plurality of walking parameters and a multiple regression analysis with a score of the emotion data as an objective variable and the plurality of walking parameters included in the walking data as explanatory variables;

when the input of the walking data is newly received, estimating the emotion of the subject from the plurality of walking parameters included in the newly received walking data based on the corresponding data; and outputting information indicating the estimated emotion of the subject, and when the emotion of the subject newly estimated from the walking data is a first emotion, identifying, from the corresponding data, a target set of walking parameters associated with a second emotion different from the first emotion;

determining a difference between the plurality of walking parameters included in the newly received walking data and the target set of walking parameters; and outputting a walking advice based on the determined difference in order to bring the walking data estimated as the first emotion closer to the walking data associated with the second emotion.

9. The emotion estimating method according to claim 8, further comprising:

when the emotion of the subject newly estimated from the walking data is a first emotion, obtaining the walking data associated with a second emotion different from the first emotion from the corresponding data, and outputting walking advice that brings the walking data estimated as the first emotion closer to the walking data associated with the second emotion.

* * * * *